United States Patent
Strickland et al.

(10) Patent No.: US 6,251,878 B1
(45) Date of Patent: Jun. 26, 2001

(54) INHIBITION OF UV-INDUCED IMMUNE SUPPRESSION AND INTERLEUKIN-10 PRODUCTION BY CYTOPROTECTIVE TAMARIND OLIGOSACCHARIDES

(75) Inventors: Faith Strickland; Ronald Pelley, both of Galveston, TX (US); Peter Albersheim; Alan Darvill, both of Athens, GA (US); Markus Pauly, Frederiksberg (DK); Stefan Eberhard, Athens, GA (US)

(73) Assignees: Board of Regents, The University of Texas System, Austin, TX (US); University of Georgia Research Foundation Inc., Athens, GA (US)

( * ) Notice: Subject to any disclaimer, the term of this patent is extended or adjusted under 35 U.S.C. 154(b) by 0 days.

(21) Appl. No.: 09/348,977

(22) Filed: Jul. 7, 1999

(Under 37 CFR 1.47)

Related U.S. Application Data

(60) Provisional application No. 60/092,444, filed on Jul. 10, 1998.

(51) Int. Cl.$^7$ .................................................. A61K 31/715
(52) U.S. Cl. ................................................................ 514/54
(58) Field of Search ................................................ 514/54

(56) References Cited

U.S. PATENT DOCUMENTS

| | | | | |
|---|---|---|---|---|
| 5,547,997 | * | 8/1996 | Kludas ................................. | 514/773 |
| 5,824,659 | | 10/1998 | Strickland et al. ..................... | 514/54 |
| 5,846,548 | * | 12/1998 | Bartos ............................... | 424/278.1 |

FOREIGN PATENT DOCUMENTS

| | | |
|---|---|---|
| 07147934 | * | 6/1995 (JP) . |
| 96/20709 | * | 7/1996 (WO) . |

OTHER PUBLICATIONS

Bauer et al., "The structure of plant cell walls II. the hemicellulose of the walls of suspension–cultured sycamore cells," *Plant Physiol.*, 51:174–187, 1973.

Keegstra et al., "The structure of plant cell walls, III. a model of the walls of suspension–cultured sycamore cells based on the interconnections of the macromolecular components," *Plant Physiol.*, 51:188–196, 1973.

Kooiman, "The constitution of tamarindus–amyloid," *Recueil*, 80:849–865, 1961.

Mastromarino et al., "Antiviral activity of natural and semi-synthetic polysaccharides on the early steps of rubella virus infection," *J. of Antimicrobial Chemotherapy*, 39:339–345, 1997.

McDougall and Fry, Inhibition of auxin–stimulated growth of pea stem segments by a specific nonasaccharide of xyloglucan, *Planta*, 175:412–416, 1988.

"Programs and Abstracts," 26$^{th}$ Annual Meeting American Society for Photobiology, Snowbird, Utah, Jul. 11–15, 1998.

Sano et al., "Lack of Carcinogenicity of tamarind seed polysaccharide in B6C3F$_1$ Mice," *Food and Chem. Toxicology*, 34:463–467, 1996.

Sergio, "A natural food, the malabar tamarind, may be effective in the treatment of obesity," *Medical Hypotheses*, 27:39–40, 1988.

Sone et al., "Inhibitory effect of oligosaccharides derived from plant xyloglucan on intestinal glucose absortion in rat," *J. Nutr. Sci. Vitaminol.*, 38:391–395, 1992.

Strickland et al., "Inhibition of uv–induced immune suppression and interleukin–10 production by plant oligosaccharides and polysaccharides," *Photochemistry and Photobiology*, 69:141–147, 1999.

Talmadge et al., "The structure of plant cell walls I. the macromolecular components of the walls of suspension–cultured sycamore cells with a detailed analysis of the pectic polysaccharides," *Plant Physiol.*, 51:158–173, 1973.

York et al., "Inhibition of 2,4–Dichlorophenoxyacetic acid–stimulated elongation of pea stem segments bya xyloglucan oligosaccharide$^1$," *Plant Physiol.*, 75:295–297, 1984.

York et al., "Structural analysis of xyloglucan oligosaccharides by $^1$H–n.m.r. spectroscoopy and fast–atom–bombardment mass spectrometry," *Carbohydrate Research*, 200:9–31, 1990.

* cited by examiner

*Primary Examiner*—William R. A. Jarvis
*Assistant Examiner*—Vickie Kim
(74) *Attorney, Agent, or Firm*—Fulbright & Jaworski L.L.P.

(57) ABSTRACT

Methods and compositions are disclosed for the prevention and/or treatment of immunological damage to skin exposed to ultraviolet irradiation. The compositions described herein include biologically active tamarind seed xyloglucan oligosaccharides obtained via treatment of tamarind xyloglucan with a fungal β-glucanase. Advantageously, the cytoprotective tamarind seed xyloglucan oligosaccharides are stable at ambient conditions. In one aspect, the composition includes an aqueous solution of tamarind seed xyloglucan oligosaccharides having a concentration of at least $10^{-6}$ μg per mL of the solution. In another aspect, the method includes preventing the suppression of delayed type hypersensitivity. In yet another aspect, the invention includes reducing the amount of interleukin-10 produced by keratinocytes in the skin.

10 Claims, 4 Drawing Sheets

15 kJ/m² UV + Methyl cellulose (no 1° Ab)

15 kJ/m² UV + Methyl cellulose 15 kJ/m² UV + Tamarind (1 µg)

15 kJ/m² UV Only 15 kJ/m² UV + oligogalacturonide (1 µg)

Ability of Oligosaccharides to Prevent UV-Induced Suppression of DTH Immune Responses to *Candida Albicans* ns. Indirect
INHIBITION OF UV-INDUCED IMMUNE SUPPRESSION AND INTERLEUKIN-10 PRODUCTION BY CYTOPROTECTIVE TAMARIND OLIGOSACCHARIDES The present application is a continuation of copending U.S. Provisional Patent Application Serial No. 60/092,444 filed Jul. 10, 1998.

The government owns rights in the present invention pursuant to grant number GA70383 from the National Institutes of Health.

BACKGROUND OF THE INVENTION

1. Field of the Invention

The present invention relates generally to protection of the immune system. More particularly, it concerns preventing or correcting immunological damage to skin exposed to ultraviolet irradiation.

2. Description of Related Art

Recent reports directed to the global depletion of ozone in the atmosphere, including the discovery of the Antarctic "hole" in the ozone layer, have focused interest in the effects of ultraviolet radiation on human health. Although some exposure to ultraviolet radiation is needed for humans to produce vitamin D, the evidence overwhelmingly shows that ultraviolet radiation exposure is related to a range of health problems. Specifically, it is well known that ultraviolet exposure causes sunburn and is involved in the induction of certain skin cancers.

In addition to these established health concerns, research has provided recent evidence suggesting that exposure to ultraviolet radiation may have detrimental effects upon a variety of immunological reactions and may decrease the immune system's ability to respond to various infectious agents. See, e. g., Kripke (1990). In particular, it is thought that ultraviolet radiation-induced injury to the skin immune system supplies a second factor necessary for the development of common skin cancers. The primary factor in the induction of skin cancer is the mutational damage done by ultraviolet radiation to the DNA of the generative cells in the skin. However these early malignant cells are thought to be eliminated by the normal functioning of the skin immune system. When the immune function of the cells in the skin is suppressed by ultraviolet radiation, the cells cannot perform their usual surveillance function and eliminate very early skin cancers.

The effect of ultraviolet radiation in suppressing the skin immune system is separate and dissociable from the grossly apparent inflammatory and irritant effects of ultraviolet radiation on the skin such as erythema (redness), edema (swelling), and hyperkeratosis (flaking or scaling). Modalities taught in the prior art for the prevention and treatment of skin inflammation and irritation do not appear to be of utility in the treatment of ultraviolet-light-induced suppression of the skin immune system. For example, Reeve et al. (1991) reported that topical application of certain ultraviolet radiation-absorbing compounds, such as certain sunscreens, were effective in preventing ultraviolet radiation-induced erythema and edema, but that some of these sunscreens failed to prevent immunosuppression in a mouse model as measured either by contact hypersensitivity or by induction of susceptibility to transplanted tumor cells. Thus prevention of irritation and inflammation did not prevent suppression of the skin immune system. This was confirmed by Von Praag et al. (1991) and Wolf et al. (1994), who reported that commercial sunscreens may not fully protect against ultraviolet radiation-induced immunological alterations. Indirect evidence for this idea was presented by Vermeer et al. (1991) by studying the immune reaction of human subjects to the contact allergen dinitrochlorobenzene. They concluded that the pigmentation levels (of either dark skinned or tanned subjects) did not appear to protect the skin immune system from the damaging effects of ultraviolet radiation (although it is well accepted that skin pigmentation protects the skin against the irritant and inflammatory effects of ultraviolet radiation).

These studies suggest that while sunscreens alone do prevent inflammation and irritation they do not provide complete prophylactic protection against the immunosuppressive effects of ultraviolet radiation. Furthermore, pharmacologic agents which are commonly and traditionally employed for the treatment of irritated and inflamed skin are without effect in treating the suppression of the skin immune system induced by exposure to ultraviolet radiation when they are applied after the injury is manifest. Andersen et al. (1992) examined in humans the effect of treatment with the four commonest anti-inflammatory agents of ultraviolet radiation-injured skin upon edema and erythema. Topically applied corticosteroids were most effective in reducing inflammation and irritation, followed respectively by indomethicin, acetylsalicylic acid (aspirin), and diphenhydramine (Benadryl®). Aspirin and Benadryl® have not been demonstrated to be capable of restoring the ultraviolet radiation-induced damage to the skin immune system. Local application of corticosteroids reduces the skin immune response, as taught by Bergstresser (1989) and many others. Although indomethacin has been demonstrated by Reeve et al. (1995) to inhibit photocarcinogenesis, this effect appears to involve both the initiation period and the promotion period of tumor development and thus is thought to be a function of a generalized anti-carcinogenesis effect rather than an effect on the skin immune system. Thus there appears to be a pattern whereby agents capable of suppressing inflammation and irritancy do not protect the skin immune system. Recognizing this dissociation of the phenomenon of inflammation/irritation from the induction of skin cancer, academic experimental dermatologists have virtually abandoned the use of erythema and edema as endpoints for the deleterious effects of ultraviolet radiation in the induction of skin cancer, and have instead adopted direct measures of carcinogenesis (e. g., mutational changes in the DNA of skin cells and direct measurement of the function of the skin immune system).

Several investigators have noted the anti-inflammatory and anti-irritant activities of Aloe materials. For example, Farkas (U.S. Pat. No. 3,103,466) disclosed the use of Aloe Vera to provide analgesic effect upon inflamed or irritated skin. However, these investigators failed to demonstrate an understanding of the difference between treatment of inflammation and irritation versus restoration of the skin immune response. For example, some inventors have viewed Aloe preparations as having utility only as sunscreens (see Baron, U.S. Pat. No. 4,788,007) and thus having utility only for prevention and not for treatment. Those inventors which appreciate the ultility of Aloe preparations for theraputic purposes seem to envision only effects that can be seen (erythema and swelling) or percieved (itching and pain). For example, those patents which directly claim relief of pain and itching (Rosenthal, U.S. Pat. No. 4,585,656 and Gruber, U.S. Pat. No. 4,593,046) offer embodiments that result in products that may be ineffective in restoring the skin immune system. Those patents concerned with processing (Maret, U.S. Pat. No. 3,878,197; Cobble, U.S. Pat. No.

3,892,853 and Coats, U.S. Pat. No. 4,178,372) which do not claim biological activity but which do refer to biological activity in the examples teach little to one skilled in the art; the examples are so vague with regard to biological activity on topical application that one would not be led to understand the difference between the treatment of inflammation and irritation versus restoration of the skin immune system. Therefore, it is not suprising that commercial Aloe products are ineffective in preventing suppression of the skin immune response by ultraviolet radiation.

Strickland et al. (1994) have investigated the ability of *Aloe barbadensis* gel extract to prevent suppression of contact hypersensitivity (CHS) and delayed-type hypersensitivity (DTH) responses in mice by ultraviolet (UV) radiation. Treatment of UV-irradiated skin with Aloe immediately after irradiation was found to prevent suppression of both CHS to fluorescein isothiocyante and DTH to *Candida albicans*. Aloe treatment did not prevent the formation of cyclobutyl pyrimidine dimers in the DNA of UV-irradiated skin or accelerate repair of these lesions. Thus, these studies demonstrated that topical application of an *Aloe barbadensis* gel extract to the skin of UV-irradiated mice ameliorates UV-induced immune suppression by a mechanism other than DNA damage or repair. However, the precise components of Aloe gel having these beneficial effects were not identified. Strickland et al. also noted that there can be marked variability with regard to sources of Aloe, variability in commercial Aloe gel extract production processes, and variability with regard to bacteriology of starting materials, all of which can contribute to the difficulty of obtaining consistent, reproducible data in studies of the biological activity of Aloe extracts. Byeon et al. (1998) have shown that Aloe contains multiple immunoprotective factors, some of which are labile, i. e., their ability to prevent immunosuppression can decay rapidly following manufacture.

Strickland et al. in U.S. Pat. No. 5,824,659 teach that the Aloe polysaccharide in its native form is biologically inactive. Upon cleavage by a crude culture supernatant of fungi termed "cellulase," this heteropoylsaccharide is cleaved into two chemically and biologically distinct fragments. The first fragment termed acemannan by McAnalley has the biological activity classically ascribed to Aloe polysaccharide, physically consists of polymers ranging in molecular weight from greater than 5,000 daltons to greater than 200,000 daltons, and chemically consists of repeating units of beta 1–4 mannan alternately 6 and 2–3 acetylated. The second product of "cellulase" cleavage consists of branch points forming the acemannan homopolymer into a gel, physically comprises oligosaccharide of under 5,000 daltons molecular weight, and chemically consists of glucose more so than mannose comprising 1, 4, and 6 linkages. U.S. Pat. No. 5,824,659 further teaches that it is this cleavage oligosaccharide which bears the cytoprotective biological activity, especially the ability to downregulate Interleukin-10 production by UVB-injured keratinocytes. U.S. Pat. No. 5,824,659, however, is silent with regard to various aspects of the present invention, which allow for maximal benefit to be derived from the invention. For example, the fresh *Aloe barbadensis* used in U.S. Pat. No. 5,824,659 is difficult to obtain commercially with desired purity and freshness (Pelley et al., Subtropical Plant Science 1999). Furthermore, U.S. Pat. No. 5,824,659 teaches that the cytoprotective oligosaccharide used in that patent is subject to further inactivating cleavage by glycosidases. Furthermore, U.S. Pat. No. 5,824,659 is silent as to how those of ordinary skill in the art could predictably find plant oligosaccahrides similar to those taught in that application and how compounds of greater potency than those taught in U.S. Pat. No. 5,824,659 may be obtained.

Clearly, there exists a need for an effective method or treatment modality for preventing or correcting immunological damage to skin exposed to ultraviolet irradiation. Such a method would ideally employ a composition including a well-characterized active ingredient having excellent chemical stability and long shelf life.

SUMMARY OF THE INVENTION

Disclosed in the present application is a novel relationship whereby prediction can be made as to which of the millions of plant oligosaccharides are likely to bear biological activity similar to the Aloe oligosaccharides taught by U.S. Pat. No. 5,824,659. Further, disclosed is the inventors' discovery that utilizing the novel insights disclosed herein, unexpected results may be obtained yielding thousand-fold or greater activities than those taught by U.S. Pat. No. 5,824,659.

Disclosed herein are methods and compositions for the prevention and/or treatment of immunological damage to skin exposed to ultraviolet irradiation. The compositions described herein include biologically active tamarind seed xyloglucan oligosaccharides obtained via treatment of tamarind xyloglucan with a fungal β-glucanase. Advantageously, the cytoprotective tamarind seed xyloglucan oligosaccharides of the present invention are stable at ambient conditions.

In one embodiment, the present invention includes a method of preventing UV-induced suppression of the immune response of the skin of an animal, the method including contacting the skin with a composition including tamarind seed xyloglucan oligosaccharides prior to exposure of the skin to UV radiation. In one aspect, the composition includes an aqueous solution of tamarind seed xyloglucan oligosaccharides having a concentration of at least $10^{-6}$ µg per mL of the solution. In another aspect, the method includes preventing the suppression of delayed type hypersensitivity. In yet another aspect, the invention includes reducing the amount of interleukin-10 produced by keratinocytes in the skin. In certain preferred aspects, the animal in this method is a human being.

In another embodiment, the present invention includes a method of treating UV-induced suppression of the immune response of the skin of an animal, the method including contacting the skin with a composition including including tamarind seed xyloglucan oligosaccharides. In one aspect, the composition includes an aqueous solution of tamarind seed xyloglucan oligosaccharides having a concentration of at least $10^{-6}$ µg per mL of the solution. In another aspect, the method includes treating and/or preventing the suppression of delayed type hypersensitivity. In yet another aspect, the invention includes reducing the amount of interleukin-10 produced by keratinocytes in the skin. In certain preferred aspects, the animal treated with the methods and compositions of the present inventions is a human being.

In yet another embodiment, the present invention is a skin emollient including tamarind seed xyloglucan oligosaccharides. In a preferred aspect, this skin emollient includes one or more suitable carriers for cutaneous application. The emollient of the present invention is further defined as suppressing a UV-induced immune response in the skin of an animal. The emollient of this invention prevents suppression of delayed type hypersensitivity and reduces the amount of an interleukin-10 produced in the skin.

In a final embodiment, the present invention resides in a method of treating UV-induced suppression of the immune response of the skin of an animal, said method comprising administering to said animal subsequent to UV exposure an effective dose of a composition comprising tamarind seed xyloglucan oligosaccharides. In certain aspects of the invention, the compostion may be administered orally or parenterally.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
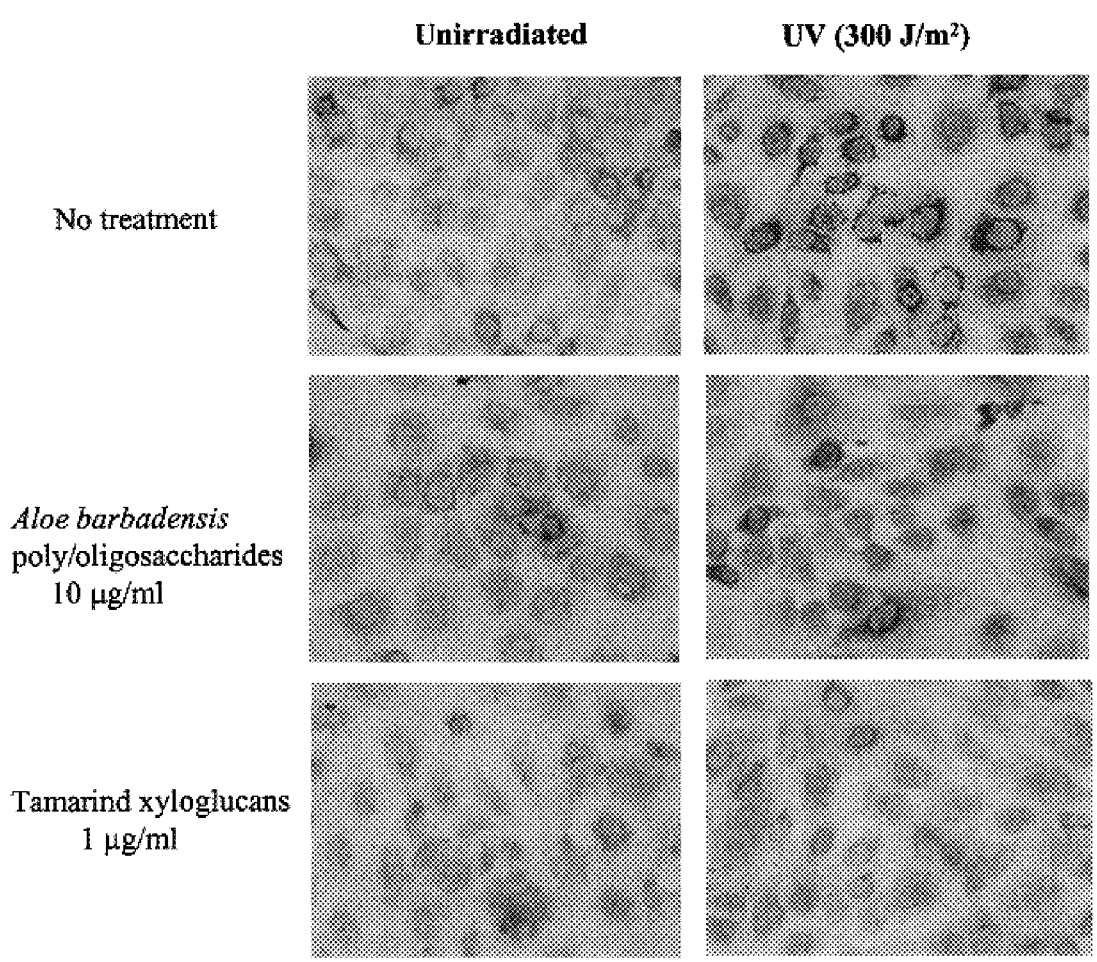
FIG. 1 shows SAPK/JNK activation in Pam 212 keratinocytes. As shown, the unirradiated cells exhibit a low background level of diffuse cytoplasmic staining. Following UV-irradiation, the phosphorylated (activated) JNK/SAPK proteins appear as a brown staining ring around the nucleus of the cells. *Aloe barbadensis* treatment partially reduced the activation (amount of staining observed.) Tamarind xyloglucan treatment of the UV-irradiated cells completely reduced the staining to background levels.

Taught herein are methods and compositions for the prevention and/or treatment of immunological damage to skin exposed to ultraviolet irradiation. The inventive compositions include biologically active tamarind seed xyloglucan oligosaccharides obtained via treatment of tamarind xyloglucan with a fungal β-glucanase. In the examples which follow, novel processes are described for the preparation of not only the claimed tamarind seed xyloglucan oligosaccharides, but for biologically active 1,4-linked α-D-oligogalacturonides which are structurally distinct from therapeutic *Aloe barbadensis* oligosaccharides previously taught. The inventors disclose that these carbohydrates, which mediate plant responses to injury, comprise a family of plant-derived polysaccharides and oligosaccharides that can regulate responses to injury in animal tissues. Comparative studies using murine models have shown that, unexpectedly, the tamarind seed xyloglucan oligosaccharides are several orders of magnitude more effective in the protection of delayed type hypersensitivity (DTH) immune response to *Candida albicans,* as compared with the 1,4-linked α-oligogalacturonides and *Aloe barbadensis* extracts. Advantageously, the cytoprotective tamarind seed xyloglucan oligosaccharides disclosed herein are stable at ambient conditions.

The concept that immune-protective carbohydrates in *Aloe barbadensis* gel were derived from cleavage of an inactive precursor molecule was put forth in U.S. Pat. No. 5,824,659 by Strickland et al. The inventors described that further cleavage or breakdown of the active poly/oligosaccharide destroys its immune-protective activity. The inventors now disclose that the carbohydrates present in *Aloe barbadensis* gel that protect the immune response against suppression by UV radiation may belong to a family of carbohydrates with regulatory activity called "oligosaccharins." See Albersheim and Darvill (1985). Briefly, Albersheim and Darvill and their associates developed the concept that oligosaccharides can have regulatory activity in plants. These investigators termed the biologically active plant oligosaccharides "oligosaccharins;" a number of different oligosaccharins from plant cell walls and have been purified and partially structurally characterized. The structural features of oligosaccharins required for biological activity in plant systems have also been investigated.

The use of carbohydrates derived from plants other than Aloe to prevent UV-induced immune suppression is an important improvement for several reasons. First, oligosaccharins and tamarind xyloglucan represent another source of carbohydrates that possess immune protective activity. Second, unlike Aloe polysaccharides, the molecular structure of many of these carbohydrates have been partially characterized and their activity in plant-based assays of biological activity have been investigated. The ability of xyloglucan oligosaccharides isolated from tamarind seeds to prevent UV radiation-induced immune suppression, as demonstrated hereinbelow, is unexpectedly very potent and can be detected using low pictogram quantities of the xyloglucan oligosaccharides applied in a saline solution to the skin of UV-irradiated mice. The fact that the tamarind xyloglucan oligosaccharides did not require a vehicle to be active has important therapeutic implications. Finally, the preservation of immune activity by carbohydrates that regulate plant responses to injury may lead to the development of a whole family of agents with therapeutic potential for cellular recovery after injury.

Potential applications contemplated for the technology disclosed herein include:

(1) Reducing the risk in humans of developing non-melanoma skin cancer by preserving the immune responses usually suppressed by UV radiation (2) Preventing the production of immunosuppressive cytokines, such as interleukin-10, following exposure of the skin to UV radiation (3) Blocking stress activated protein kinase and Janus kinase (SAPK/JNK) signal transduction pathways activated by UV radiation and, potentially, other environmental stimuli.

Potential products based on the technology disclosed herein include:

(1) New generations of post-sun exposure skin care products that are designed to reduce the risk of developing non-melanoma skin cancer (2) Therapeutic agents that aid in cellular recovery after injury, e. g. after radiation treatment, surgery, or chemotherapy (3) Therapeutic agents that are aimed at regulating the activation of SAPK/JNK cellular signal transduction pathways Formulation of Skin Creams, Sun Screens, and Related Products Containing Emollients Based on Tamarind Seed Xyloglucan Oligosaccharides It is contemplated that various skin creams, sun screens, ointments, lotions, foams, and related skin care products may be formulated from the tamarind seed xyloglucan oligosaccharides of the present invention. In this regard, various materials have been taught in the art for use as excipients and as agents that condition the skin. In general, such conditioning agents may help make the skin feel soft, smooth, silky and moisturized, in addition to having a preventative or therapeutic effect as detailed elsewhere herein. The term "moisturizer" is often used synonymously with the term emollient, and is meant to describe a material which imparts a soft, smooth, silky and moisturized feeling to the skin surface. Of course, water will be an important ingredient of most skin care formulations based on the oligosaccharides of the invention.

One way of moisturizing is to reduce the rate of water loss from the stratum corneum (skin surface) by depositing an occlusive material (emollient or emulsifier) on the skin surface which prevents water evaporation. Another technique is to add hygroscopic nonocclusive substances (humectants), which will retain water to the stratum corneum, making water available to the skin surface thereby producing the desired cosmetic effect. Nonocclusive moisturizers also function by improving the lubricity of the skin. Both occlusive and nonocclusive moisterizers as well as mixtures thereof are operative in the present invention. Examples of occulusive moisturizers. (emollients or emulsifiers) include, lanolin and its derivatives, long chain esters, waxes, saturated and unsaturated fatty alcohols, conditioning oils and extracts, phospholipids, sterols, ceramides and silicones. Examples nonocculusive moisturizers (humectants) include polyols, fatty acids, certain alkanolamides, pyrrolidone carboxylic acid and their derivatives. It is to be understood that any such skin conditioning agent or mixtures thereof can be employed herein, depending on the formulations desires.

Examples of lanolin derivatives useful in the present invention include, but are not limited to lanolin, lanolin oil, lanolin fatty acid, sodium lanolate, potassium lanolate, ammonium lanolate, monoethanolamine lanolate, diethanolamine lanolate, triethanolamine lanolate, lanolin alcohol, acetylated lanolin, acetylated lanolin alcohol, ethoxylated lanolin such as PEG-75 lanolin, propoxylated/ethoxylated lanolin oil such as PPG-12/PEG-65 lanolin oil, ethoxylated sorbitol lanolin, propoxylated lanolin, ethoxylated lanolin alcohol, lanolin alcohol ricinoleate, lanolin alcohol linoleate, acetate of lanolin alcohol ricinoleate, hydrogenated lanolin, ethoxylated hydrogenated lanolin and the like.

Examples of long chain esters useful in the present invention include, but are not limited to cetyl acetate, stearyl acetate, oleyl acetate, lauryl lactate, myristyl lactate, cetyl lactate, stearyl lactate, decyl neopentanoate, myristyl propionate, decyl oleate, isopropyl myristate, lauryl myristate, myristyl myristate, myreth-3-myristate, palmityl myristate, stearyl myristate, isopropyl palmirate, octyl palmitate, 2-ethylhexyl palmitate, lauryl palmitate, myristyl palmirate, palmityl palmitate, stearyl palmirate, butyl stearate, myristyl stearate, palmityl stearate, isocetyl stearate, isostearyl isostearate, oleyl myristate, oleyl stearate, oleyl oleate, methyl cocoate, isopropyl cocoate, butyl cocoate, cetearyl octanoate; butyloxyethyl stearate, isopropyl lanolate, cetyl octanoate, coconut caprate/caprylate, hydroxyoctacosanyl hydroxystearate, cetyl ricinoleate, decyl oleate, butyl oleate, octyliauryl myristate, PPG-2 myristyl ether propionate, PPG-10 butanediol, PPG-8-C12-C20 alkyl ester, Peg-45 palm kernel glyceride, neopentylglycol dicaprylate/dicaprate, C12-C15 alcohol benzoate, diisoarachidyl dilinoleate, dioctyl maleate, ascorbyl palmitate, diisopropyl adipate, diisohexyl adipate, dihexadecyl adipate, diisopropyl sebacate, dioctyl succinate, didecyl succinate, jojoba esters and the like.

Examples of waxes useful in the present invention include, but are not limited to beeswax, white beeswax, polyoxyethylene sorbitol beeswax, paraffin wax, ceresin wax, lanolin wax, polyethylene wax, microcrystalline wax, spermaceti, carnauba wax, candelilla wax, wool wax alcohols, petroleum wax, ozokerite wax, glyceride wax, castor wax, emulsifying wax polydecene and the like.

Examples of saturated and unsaturated fatty alcohols useful in the present invention include, but are not limited to carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol and the like.

Examples of conditioning emollient oils useful in the present invention include arnica blossom oil, apricot kernel oil, avocado oil, babassa oil, balm mint oil, basil oil, bergamot oil, bitter almond oil, bitter orange oil, castor oil, calendula oil, coconut oil, collagen/lanolin oil, cod liver oil, cucumber oil, corn oil, carrot oil, egg oil, eucalyptus oil, evening primrose oil, geranium oil, gardenia oil, grapefruit oil, grape seed oil, hybrid safflower oil, jasmine oil, jojoba oil, kiwi oil, light mineral oil, lemon oil, mandarin orange oil, orange flower oil, orange oil, mink oil, olive oil, palm oil, peach kernel oil, passionflower oil, rapeseed oil, sesame oil, soybean oil, safflower oil, sunflower oil, sweet almond oil, vegetable oil, wheat germ oil, petrolatum, squalene, squalane, ozokerite, hydrogenated castor oil, hydrogenated sunflower seed oil, hydrogenated peanut oil, hybrid sunflower seed oil, borage oil, PEG-40 hydrogenated castor oil and the like.

Examples of conditioning extracts useful in the present invention include aloe extract, aloe flower extract, aloe vera gel extract, apple extract, apple leaf extract, apple pectin extract, balsam canada extract, balsam oregon extract, balsam peru extract, balsam tolu extract, balm mint extract, black walnut extract, birch leaf extract, birch sap extract, calendula extract, chamomile extract, colocynth extract, comfrey extract, comfrey leaf extract, coltsfoot extract, clover blossom extract, custard apple extract, egg extract, fennel extract, gelatin extract, geranium extract, grapefruit extract, horsetail extract, henna extract, hazel extract, hops extract, honey extract, indian cress extract, kelp extract, lemon extract, lemon juice extract, lemon peel extract, lime extract, malt extract, mandarin orange extract, matricaria extract, mint extract, nettle extract, oakmoss extract, orange extract, orange peel extract, ponkan extract, papaya extract, pummelo extract, red raspberry extract, red raspberry leaf extract, rhubarb extract, rosemary extract, thyme extract, tamarind extract, tangerine extract, sage extract, strawberry extract, strawberry leaf extract, valerian extract, witch hazel extract, autolyzed yeast extract, yarrow extract, thistle extract, passion fruit extract, ivy extract, seaweed extract, aqua hamamelis and the like.

Suitable phospholipids are exemplified as complex fat soluble substances that contain in their molecule, in addition to fatty acids and glycerol, a nitrgenous base such as choline or ethanolamine, two long alkyl chains having about 10 to about 18 carbon atoms and phosphoric acid. These compounds are found universally in living cells and are either completely absent or present in low concentrations in surface lipids. Specific examples of phospholipids useful in the present invention include, but are not limited to lecithin, cephalin (phosphatidylethanolamine), phosphatidylinositol and the like.

Examples of sterols useful in the present invention include, but are not limited to cholesterol, ethoxylated cholesterol, propoxylated cholesterol, cholesteryl acetate, cholesteryl benzoate, cholesteryl heptanoate, cholesteryl octanoate, cholesteryl nonanoate, cholesteryl palmirate, cholesteryl stearate, cholesteryl oleate, cholesteryl linoleate, cholesteryl oleyl carbonate, cholesteryl hydrocinnamate, cholesteryl chloride, 7-dehydrocholesterol, lumisterol, tachysterol, pyrocalciferol, lanosterol, lathosterol, ergosterol, stigmasterol, sitosterol, asterosterol, PEG-25 soya sterol and the like.

Both natural ceramides (sphingolipids) and synthetic pseudoceramides may be of use in the practice of the present invention, however the synthetic pseudoceramides are preferred because they are relatively cheaper to produce. Examples of ceramides or pseudoceramides that are useful in the present invention include, but are not limited to ceramide 1, ceramide 2, ceramide 3, ceramide 4, ceramide 5, ceramide 6, ceramide 7, lactosyl ceramide, ceramide trihexoside (globotriosyl ceramide), globoside (globotetraosyl ceramide), sphingomyelin, psychosine (ceramide galactoside), kerasin (ceramide galactoside with an amidated fatty acid), phrenosin (ceramide galactoside with an amidated 2-hydroxy fatty acid), bovine sulfatide (ceramide galactoside 3-sulfate with an amidated fatty acid), glucocerebrosides (ceramide glucoside), gangliotetraosyl ceramide, monosialoganglioside, disialoganglioside, trisialoganglioside, N-(2-hydroxyoctadecyl)-N-(2-hydroxyethyl)-2-hydroxyhexadecamide, N-(2-hydroxyoctadecyl)-N-(2-O-glucopyranosyl)ethyl-2-hydroxyhexadecamide, N-(2-hydroxyoctadecyl)-N-(2-hydroxyethyl)-2-hydroxy-omega-O-linoleoyldocosamide, N-(2-hydroxyoctadecyl)-N-(2-hydroxyethyl)-2-hydroxy-omega-O-linoleoylhexadecamide, N-(2,3-dihydroxyoctadecyl)-N-(2-hydoxyethyl)-2-hydroxyhexadecamide, N-(2,3-dihydroxyoctadecyl)-N-(2-hydroxyethyl)-2-hydroxy-omega-O-linoleoyldocosamide, N-(2-hydroxyoctadecyl)-N-(2-sulphoethyl)-2-hydroxyhexadecamide, N-(2-hydroxyoctadecyl)-N-(2-phosphoethyl)-2-hydroxyhexadecamide, N-(2,3-dihydroxypropyl)-N-dodecyl hexadecanamide, N-(2,3-dihydroxypropyl)-N-tetradecyl hexadecanamide, N-(2,3-dihydroxypropyl)N-hexadecyl hexadecanamide, N-(2,3-dihydroxypropyl)-N-octadecyl hexadecanamide, N-(2,3-dihydroxypropyl)-N-hexadecyl octanamide, N-(2,3-dihydroxypropyl)-N-dodecyl-2-hydroxyhexadecanamide, N-(2,3-dihydroxypropyl)-N-hexadecyl-2-hydroxyhexadecanamide, N-(2-hydroxy-3-hexadecyloxylpropyl)-N-(2-phosphoethyl) hexadecamide, N-(2-hydroxyoctadecyl)-N-(2-sulphoethyl) hexadecamide, N-(2-hydroxy-3-hexadecyl-oxypropyl)-N-(2-phosphoethyl)-omega-O-linoleoyldocosamide and mixtures thereof.

Suitable non-volatile silicone fluids are exemplified as polyalkylsiloxane, polyarylsiloxane, polyalkylarylsiloxane and polyethersiloxane copolymers. Mixtures of these fluids may also be used and are preferred in certain executions. The silicone fluid should be insoluble in the personal product matrix and present as a dispersion. Examples of non-volatile polyethersiloxane copolymer fluids useful in the present invention include, for example, the polyethylene oxide modified dimethylpolysiloxanes (dimethicone copolyol), polypropylene oxide modified dimethylpolysiloxanes and polyethylene oxide/polypropylene oxide modified dimethylpolysiloxanes, simethicone, cyclomethicone, cetyl dimethicone and mixtures thereof.

Other silicone materials useful in the present compositions may include silicone gums, such as high molecular weight polydiorganosiloxanes having a mean molecular weight from about 200,000 to about 1,000,000. Specific examples of silicone gums include polydimethylsiloxane, (polydimethylsiloxane)(methylvinylsiloxane) copolymer, poly(dimethylsiloxanediphenyl)(methylvinylsiloxane) copolymer and mixtures thereof.

Examples of polyols useful in the present invention include, but are not limited to propylene glycol (PG), dipropylene glycol, pentapropylene glycol, polypropylene glycol 2000 to 4000, polypropylene glycol 2000 to 4000 fatty acid esters, polyoxyethylene/polyoxypropylene glycols, polyoxypropylene/polyoxyethylene glycols, ethylene glycol, diethylene glycol, diethylene glycol mono/di-fatty acid esters, polyethylene glycol 200 to 6000 (PEG), polyethylene glycol 200 to 6000 mono/di-fatty acid esters, methoxy polyethylene glycol 350 to 5000, ethylene glycol mono/di-fatty acid esters, glycerol (glycerin), ethoxylated glycerol, propoxylated glycerol, glycerol mono/di/tri-fatty acid esters, polyglycerol, polyglycerol mono/di-fatty acid esters, erythritol, xylitol, sorbitol, sorbitan, ethoxylated sorbitol, hydroxypropyl sorbitol, mannitol, lactitol, hydrogenated starch hydrolyzates, 1,3-butylene glycol, 1,3-butylene glycol mono/di-esters, 1,2,6-hexane-triol, 2-ethyl-1,3-hexanediol, C15–C18 vincinal glycol, trimethanolethane, trimethyl-olpropane, ethoxylated trimethylolpropane, pentaerythritol, ethoxylated pentaerythritol, fructose, dextrin, glucose and the like. Preferred polyols are propylene glycol, propylene glycol stearate, propylene glycol dipelargonate, PEG-55 propylene glycol oleate, PEG-75, PEG-150, PEG-400, PPG-5 ceteth-20, ethylene glycol monostearate, ethylene glycol distearate, PEG-6 stearate, PEG-8 distearate, PEG-25 stearate, PEG-100 stearate, PEG-150 distearate, PEG-400 stearate, glycerin, diglycerin, decaglyceryl diisostearate, glyceryl laurate, glyceryl myristate, PEG-26 glycerate, caprylic/capric triglyceride, pentaerythrityl tetralaurate, sorbitan stearate, glycereth-7 and mixtures thereof.

Examples of fatty acids useful in the present invention include, but are not limited to pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, coconut fatty acid, soya fatty acid, tallow fatty acid, tall oil fatty acid, castor fatty acid, corn fatty acid, cottonseed fatty acid, palm fatty acid, rapeseed fatty acid, safflower fatty acid, sesame fatty acid, sunflower fatty acid and the like.

Examples of hygroscopic alkanolamides useful in the present invention include, but are not limited to acetamide MEA, acetamide DEA, lactamide MEA, lactamide DEA, lactaglucamide, lactamethylglucamide and the like.

Example of pyrrolidone carboxylic acids useful in the present invention include but are not limited to sodium, potassium, ammonium and alkanol ammonium salts of pyrrolidone carboxylic acid, ethyl pyrrolidone carboxylic acid and the like. Typical levels of skin conditioning agent may be from about 1% to about 40% by weight.

Any suitable thickening agent may be used in formulating the skin care products based on the present invention.

Various materials have been taught in the art as auxiliary thickening agents, which are useful in combination with heteroatom containing alkyl aldonamide compounds of the present invention for enhancing viscosity and rendering the composition more acceptable. Examples of common thickening agents include fumed silica, bentonite (hydrated aluminum silicone dioxide), PEG 55 propylene glycol oleate, PEG 6000 distearate and the like.

It is important to recognize that certain natural polymers, including cellulose, may bind strongly with the tamarind xyloglucan oligosaccharides of the present invention, making them less effective upon application than they might otherwise be. For this reason, thickening agents such as cellulose and related carbohydrate materials which strongly bind the oligosaccharides disclosed herein may be incompatible with the formulations of the present invention.

Examples of sunscreens or UV absorbers useful in the present invention which protect the skin and certain sensitive ingredients from harmful sunlight include dipropyleneglycol salicylate, octyl salicylate, 2-ethylhexyl p-dimethylaminobenzoate (octyldimethyl-PABA), polyoxyethylene p-dimethylaminobenzoate (PEG-25 PABA), Tri-PABA-panthenol, dromtrizole, 2-ethylhexyl p-methoxycinnamate, DEA p-methoxycinnamate, butyl methoxybenzoylmethane, benzophenones 1 through 12 particularly, 2,4-dihydroxybenophenone (benzophenone 1), 2,2',4,4'-tetrahydroxybenzophenone (benzophenone 2), 2-hydroxy-4-methoxybenzophenone (benzophenone 3), 2-hydroxy-4-methoxybenzophenone-5-sulfonic acid (benzophenone 4), 2,2'-dihydroxy-4,4'-dimethoxybenzophenone (benzophenone 6), 2,2'-dihydroxy-4-methoxybenzophenone (benzophenone 8), disodium 2,2'-dihydroxy-4,4'-dimethoxy-5,5'-disulfobenzophenone (benzophenone 9), 2-hydroxy-4-n-octoxybenzophenone, methyl anthranilate, 2-(2-hydroxy-5'-methylphenyl)benzotriazole, 2-phenylbenzimidazole-5-sulfonic acid, 2-hexanolethyl salicylate, octyl methoxycinnamate, butyl metoxydibenzoylmethane, ethyl p-amino benzoate and mixtures thereof.

Examples of vitamins useful in the present invention which provide the hair with valuble nutrition include vitamin A (as retinyl acetate, propionate or palmitate) provitamin A (based on carrot extract, as beta-carotene), vitamin B1 (as thiamine mononitrate), vitamin B2 (as riboflavin), vitamin B3 (as niacinamide), vitamin B5 (as pantothenic acid), provitamin B5 (as panthenol), vitamin B6 (as pyridoxine hydrochloride, dioctenoate, dilaurate, dipalmitate or tripalmitate), vitamin B12 (as cyanocobalamin), vitamin B15 (as pangamic acid), vitamin C (as ascorbic acid), vitamin D2 (as ergocalciferol), vitamin D3 (as cholecalciferol), vitamin E (as dl-alpha-tocopherol acetate, linoleate or nicotinate,), vitamin F (as glyceryl linoleate and glyceryl linolenate), vitamin K1 (as phytonadione), vitamin K3 (as menadione), paba (p-aminobenzoic acid), choline, folic acid, biotin, allantoin biotin, retinol, inositol, allantoin calcium pantothenate, licithin (choline di-C16-C18 glycerophosphate), cholesterol, PEG 16 soya sterol, bisabolol, bioflavoniod and mixtures thereof; provitamin A, vitamin B1, vitamin B2, provitamin B5, vitamin B6, vitamin B12 and vitamin E.

Examples of amino acids useful in the present invention which provide the skin with valuble nutrition include alanine, beta-alanine, N-methylalanine, N-phenylalanine, alpha-aminoisobutyric acid, alpha-aminobutyric acid, alpha-aminocaproic acid, epsilon-aminocaproic acid, glycine, N-ethylglycine, N-propylglycine, N-butylglycine, leucine, methionine, derivatives of methionine, sarcosine, serine, norvaline, tryptophan, lysine, aspartic acid, glutamic acid, iminodiacetic acid, keratin amino acids (keratin polypeptides), silk amino acids, allantoin acetyl methionine, allantoin, deoxyribonucleic acid, protamine/nucleic acid complex, nucleic acid, collagen amino acids, retinyl palmitate polypeptide, proline, polyglucan and mixtures thereof; glycine, methionine, sarcosine, keratin amino acids and silk amino acids.

Examples of proteins useful in the present invention which provide the skin with valuble nutrition include hydrolyzed casein, hydrolyzed collagen (hydrolyzed animal protein), myristoyl hydrolyzed animal protein, hydrolyzed corn protein, hydrolyzed glycosaminoglycans, hydrolyzed keratin (keratin protein), hydrolyzed milk protein, hydrolyzed pea protein, hydrolyzed potato protein, hydrolyzed rice protein, hydrolyzed silk (silk protein), hydrolyzed soy protein, hydrolyzed vegetable protein, hydrolyzed wheat gluten, hydrolyzed wheat protein, hydrolyzed yeast protein and mixtures thereof. Preferred proteins are hydrolyzed collagen, hydrolyzed keratin protein, hydrolyzed silk protein, hydrolyzed soy protein, TEA coco hydrolyzed animal protein, potassium coco hydrolyzed animal protein, propyltrimonium hydrolyzed collagen and hydrolyzed animal elastin.

Pharmaceutical Compositions and Routes of Administration of Tamarind Seed Xyloglucan Oligosaccharides-Based Therapeutic Agents It is contemplated that the tamarind seed xyloglucan oligosaccharides of the present invention may have protective activity when administered orally or parenterally. In this regard, pharmaceutical compositions of the instant invention comprise an effective amount of at least tamarind xyloglucan oligosaccharides dissolved or dispersed in a pharmaceutically acceptable carrier, such as a pharmaceutically acceptable buffer, solvent or diluent, or aqueous medium. The phrases "pharmaceutically acceptable" or "pharmacologically acceptable" refer to molecular entities and compositions that do not produce an adverse, allergic or other untoward reaction when administered to a human. As used herein the terms "pharmaceutically acceptable carrier" and "pharmaceutically acceptable buffer, solvent or diluent" include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

As used herein the terms "contact", "contacted", and "contacting", are used to describe the process by which an effective amount of a pharmacological agent, e. g., any of the compounds disclosed in the present invention, comes in direct juxtaposition with the target tissue or cells.

For methods of treating mammals, pharmaceutical compositions may be administered by a variety of techniques, such as parenteral, topical or oral administration. For example, the compositions of the instant invention may also be formulated for parenteral administration, e.g., formulated for injection via the intravenous, intramuscular, subcutaneous, or even intraperitoneal routes. The preparation of an aqueous composition that contains one of the inventive compounds as an active ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be employed; and the preparations can also be emulsified.

Solutions of the inventive compositions as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters. Sterile powders for the extemporaneous preparation of sterile injectable solutions or dispersions may also be useful. In all cases the form must be sterile and must be fluid to the extent that easy syringability exists. It must be stable under the conditions of manufacture and storage and must be preserved against the contaminating action of microorganisms, such as bacteria and fungi.

The compositions of the instant invention may also be formulated into a composition in a neutral or salt form. Pharmaceutically acceptable salts include the acid addition salts (formed, e.g., with any free amino groups present), which are formed with inorganic acids such as, for example, hydrochloric or phosphoric acids, or such organic acids as acetic, oxalic, tartaric, mandelic, and the like. Salts formed with any free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compounds of the present invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variations in dosage will necessarily occur depending on the condition of the subject being treated. The person responsible for administration will, in any event, determine the appropriate dose for the individual subject.

Ability of Tamarind Seed Xyloglucan Oligosaccharides to Prevent Suppression of Delayed Type Sensitivity Responses in Mice by Ultraviolet Radiation The results of in vitro and in vivo studies presented hereinbelow describe work which has been repeated more than three times, and in some cases many more times.

Briefly, the studies detailed in the examples which follow include an examination of the ability of purified plant poly- and oligosaccharides to regulate the cutaneous immune response to ultraviolet (UV) radiation and the production of immunosuppressive interleukin-10 (IL-10). C3H mice were exposed to 5 kJ/m$^2$ UVB radiation from unfiltered FS40 sunlamps and treated with between 1 pg and 10 μg tamarind xyloglucan oligosaccharides saline. The mice were sensitized three days later with *Candida albicans*. Tamarind xyloglucan oligosaccharides completely prevented UV-induced suppression of DTM responses and was effective at low pg doses. In contrast, methylcellulose and dextran control studies showed no effect on immune suppression at any dose used. Tamarind xyloglucan oligosaccharides and Aloe poly/oligosaccharides also preserved immune responses to alloantigen in mice exposed to 15 kJ/m$^2$ UVB radiation.

To assess the effect of xyloglucan on keratinocytes, murine Pam212 cells were exposed to 300 J/m$^2$ UVB radiation and treated 1 h with tamarind xyloglucan. After 24 h, the culture supernatants were collected and their IL-10 content was measured by ELISA. Tamarind xyloglucan oligosaccharides treatment of UV-irradiated cultures reduced (by approximately 50%) IL-10 protein compared with the cells treated with UV radiation alone. Tamarind xyloglucan oligosaccharides also blocked UV-activated phosphorylation of SAPK/JNK, which are important proteins in the cascade transducing cellular stress signals. Significantly, these results indicate that animal cells, like plants may use carbohydrates to regulate responses to environmental stimuli.

Numerous studies remain to be done, including (a) identification of the active oligosaccharide using a purified or synthetic molecule (the tamarind xyloglucan used in the present studies is a mixture of several molecular species); (b) identification of the cellular receptor that binds the oligosaccharin; (c) identification of the tissue target of the oligosaccharin's action (keratinocytes, antigen presenting cells, other); (d) identification of the mammalian analogs of oligosaccharins to determine the role of these molecules in animal cells' functions (oligosaccharins are regulatory molecules in plants); and (e) determination of toxicology; and (f) assessment of efficacy in human cells in vitro and in vivo.
Purification and Characterization of Biologically Active 1,4-Linked α-D-Oligogalacturonides Treatment of plant cell walls or polygalacturonic acid (PGA) with acid or enzymes releases linear oligosaccharides composed of (1→4)-linked α-D-galactosyluronic acid residues (oligogalacturonides) (Hahn et al., 1981; Nothnagel et al., 1983; Davis et al., 1986). Partially purified oligogalacturonides have been shown to elicit defense responses and morphogenetic changes in plants (Darvill et al., 1992; Ryan and Farmer, 1991). Many of those biological effects are maximally induced by preparations enriched in oligogalacturonides of dp 10 to 15, which the inventors refer to as bioactive oligogalacturonides (Darvill et al., 1992). However, none of those fractions were homogenous. Thus, there is a need to develop a method for the preparation of pure oligogalacturonides of dp 10 to 15 to demonstrate that these homogeneous fragments are indeed bioactive.

PGA, a commercial product obtained by chemical deesterification of citrus pectin, has been the material of choice for generating bioactive oligogalacturonides (Hahn et al., 1981; Nothnagel et al, 1983; Davis et al, 1986). However, each bioactive oligogalacturonide of dp between 10 and 15 accounts for only a small proportion of the compounds generated by either chemical or enzymatic fragmentation of PGA (Hahn et al., 1981; Nothnagel et al., 1983; Davis et al., 1986). Additional products include oligogalacturonides containing galactaric acid, the C-1 oxidized derivative of galacturonic acid, at their reducing end (Davis et al, 1986). The modified and unmodified oligogalacturonides are not resolved by low-pressure anion-exchange and gel-permeation chromatographies (Davis et al., 1986). Thus, it was apparent that the purification of milligram quantities of homogeneous oligogalacturonides requires the combination of high capacity and high resolution chromatographic procedures.

The inventors now describe a procedure, based on selective NaOAc-ethanol precipitation, Q-Sepharose fast-flow anion-exchange chromatography (Q-Sepharose), and semi-preparative high-performance anion-exchange chromatography with pulsed amperometric detection (HPAEC-PAD), for the purification of milligram quantities of homogeneous, bioactive oligogalacturonides.

Optimizing the enzymic generation of oligogalacturonides with dp 10 and 15. The optimal conditions for generating bioactive oligogalacturonides (dp 10 and 15) were determined by HPAEC-PAD analysis of the products released at given time intervals during a-(1→4) endopolygalacturonase (EPG) digestion of PGA. Portions (1 mL) of the digest were removed after 2, 4, 6, 8, 10, and 20 h and then immediately autoclaved (15 min at 121° C.) to inactivate the EPG. The relative proportions of oligogalacturonides (dp 10 and 15) was obtained by treating PGA with EPG for 8 h. At longer times the majority of the oligogalacturonides were enzymically fragmented to biologically inactive fragments (dp<10).

Isolation and partial characterization of the minor components present in the EPG digest of PGA. The tridecagalacturonide-containing fraction, prepared by partial EPG digestion of PGA followed by QAE-Sephadex and Q-Sepharose chromatographies (Hahn et al.), was shown, by HPAEC-PAD, to contain significant amounts (30% w/w) of modified oligogalacturonides. The components of the tridecagalacturonide-containing fraction were isolated by semipreparative HPAEC-PAD using a NaOAc, pH 8, concentration gradient (550–700 mM). These compounds were structurally characterized by glycosyl-residue and glycosylinkage composition analyses, FABMS, and $^1$H NMR spectroscopy.

Negative-ion FABMS of the major component in the tridecagalacturonide-containing fraction gave a signal m/z 2305 corresponding to [M–H]$^-$ from an oligosaccharide containing 12 galactosyluronic acid residues and galacturonic acid. The $^1$H NMR spectrum of peak II contained signals for anomeric protons (Tjan et al., 1974; Ló and van Halbeek) at δ 5.23 (H-1 reducing α-GalpA), δ 5.10 (H-(1→4)-linked α-GalpA), and δ 4.64 (H-1 reducing β-GalpA) Glycosyl-residue and glycosyl-link of terminal reducing GalpA and 4-linked GalpA in the ratio of 1.0:12.4. Thus, the component in peak II is the tridecagalacturonide.

Three components in the tridecagalacturonide-containing fraction were identified as oligosaccharides containing between 8 and 10 galacturonic acid residues with galactaric acid at their reducing ends. Negative-ion FABMS of peak V gave a signal at m/z 1617 corresponding to [M–H]$^-$ from an oligosaccharide containing eight galactosyluronic acid residues and hexaric acid. No anomeric signals form a reducing galactosyluronic acid residue were present in the $^1$H NMR spectrum of peak V. The hexaric acid was shown by glycosyl-residue and glycosyl-linkage composition analyses to be a 4-linked galactaric acid. Negative-ion FABMS of peak VIII gave signals at m/z 1793 and 1969 which correspond to [M−H] from oligosaccharides containing nine galactosyluronic acid residues and galactaric acid, and ten galactosyluronic acid residues and galactaric acid, respectively. Galactaric acid, the C-1 oxidized derivative of galacturonic derivative of galacturonic acid, may have been formed during the commercial preparation of polygalacturonic acid or may be a naturally occurring component of pectin, as a known plant oxidase converts the reducing end galacturonic acid residue of oligogalacturonides into galactaric acid (Pressey, 1993). Oligosaccharides composed of galactaric acid and between two and four 4-linked galactosyluronic acid residues have been generated by EPG treatment of poly-galacturonic acid and shown to activate the oxidation of indole-3-acetic acid by tomato peroxidase (Pressey, 1991). In contrast, the results of preliminary studies have indicated that the modified oligogalacturonides isolated in this study do not possess biological activity, as they do not induce phytoalexin accumulation in soybean hypocotyls (Hahn et al., 1981; Nothnagel et al., 1983).

The tridecagalacturonide-containing fraction was also shown to contain an oligogalacturonide with tetraric acid at its reducing end. Negative-ion FABMS of peak VII gave an ion at m/z 1556 corresponding to [M−H]− from an oligosaccharide containing eight galactosyluronic acid residues and tetraric acid. Tetraric acid is a four-carbon analogue of galactaric acid.

Two additional components in the tridecagalacturonide-containing fraction were shown, by FABMS, to have molecular weights corresponding to oligosaccharides containing only glycosyluronic acid residues. However, these compounds did not cochromatograph with their corresponding oligogalacturonides. Peak III contains a tridecauronide, and peak IV a dodeca- and a trideca-uronide. These oligohexuronides must contain at least one component that is not a (1→4)-linked α-D-galactosyluronic acid. Since the CarboPac PA-1 column is efficient in separating epimeric mixtures of oligosaccharides (Hardy et al., 1988; Lee, 1990), these oligouronides may contain one or more epimerized galactosyluronic acid residues. The alkaline conditions used during the commercial de-esterification of citrus pectin may have catalyzed epimerization (C-2 epimer, talosyluronic acid; C-3 epimer, glucosyluronic acid; C-4 epimer, glucosyluronic acid; C-5 epimer, L-altrosyluronic acid). Another possibility is that the modified oligogalacturonides contain a differently linked galactosyluronic acid residue. The structural characterization of these modified oligogalacturonides was not further pursued.

Selective, size-specific precipitation of oligogalacturonides with NaOAc and ethanol. The presence of significant quantities of modified oligogalacturonides in the oligogalacturonide-containing fractions isolated by low-pressure anion-exchange chromatography necessitated the development of a procedure for their removal on a large scale. Polysaccharides in aqueous solution can be precipitated by the addition of salt and ethanol (Roden et al., 1972). Therefore, the ability of ethanol and NaOAc to precipitate oligogalacturonides based on size and structural differences was investigated.

Solutions of EPG-digested PGA, pH 5, were treated with different concentrations of NaOAc and ethanol. The resulting precipitates and supernatants were analyzed by HPAEC-PAD, using a CarboPac column that had been calibrated with standard oligogalacturonides, to determine the relative abundance of each oligogalacturonide. The addition of 11% ethanol and 50 mM NaOAc yielded a precipitate enriched in the bioactive oligogalacturonides. Under these conditions the precipitate was enriched in oligogalacturonides of dp 8 to 25. The supernatant which was enriched in galacturonic acid and oligogalacturonides of dp 2 to 7 also contained small amounts of oligogalacturonides with dp 8 to 10 as well as additional components that did not cochromatograph with the standard oligogalacturonides; these components were not characterized but are believed to be modified oligogalacturonides. Thus, the fractional precipitation of the EPG-digested products with ethanol and NaOAc is a rapid and efficient large-scale method for obtaining materials enriched in bioactive oligogalacturonides.

Separation of the ethanol-precipitated oligogalacturonides on Q-Sepharose. A portion of the NaOAc-ethanol-precipitated oligogalacturonides (450 mg galacturonic acid equivalents) in 300 mM ammonium formate, pH 6.5 (50 mL), was fractionated by Q-Sepharose chromatography. This anion-exchange matrix, which has a high-loading capacity, does not fully resolve oligogalacturonides with a dp>9. Thus, relatively large amounts (~15 mg of each oligomer) of size-enriched oligogalacturonides with dp 10 to 15 were obtained by a single chromatographic run on the Q-Sepharose. The compositions of the pooled peaks were determined by HPAEC-PAD using a CarboPac column calibrated with standard oligogalacturonides. Each pool analyzed contained a major component that accounted for ~80% of the material. In addition, two and sometimes three minor components were present.

Purification of the Q-Sepharose-isolated oligogalacturonides by semipreparative HPAEC-PAD. The semipreparative CarboPac PA-1 column is able to fully resolve mixtures containing homogalacturonides up to at least 16 and their corresponding modified oligogalacturonides. However, this column has a loading capacity of less than 6 mg for the oligogalacturonides in the pooled Q-Sepharose peaks. A portion of the Q-Sepharose tridecagalacturonide-enriched pool (5 mg) was fractionated by semipreparative HPAEC-PAD using a KOAc, pH 8, concentration gradient. The cation used as the eluting buffer is important, as it greatly influences the solubility of the oligogalacturonides. The inventors found that the solubility of oligogalacturonides in aqueous salt solutions decreases in the order $NH_4OAc>KOAc>NaOAc$. The recovery of oligogalacturonides was less than 50%, and the oligogalacturonides often precipitated in the sample collection tubes when the CarboPac column was eluted with NaOAc, pH 8.

Ammonium-containing eluants were found to interfere with the electrochemical detection of carbohydrates. Thus, ammonium acetate is not a suitable eluant for HPAEC-PAD.

Oligogalacturonides are also soluble in potassium oxalate, a salt compatible with PAD (Hotchkiss and Hicks, 1990). However, potassium oxalate is not easily removed from the oligogalacturonides, a factor that limits its use in isolating oligogalacturonides for biological studies.

KOAc was found to give satisfactory resolution of the oligogalacturonides. Furthermore, these components were recovered in yields greater than 80% from the CarboPac column. Therefore, a concentration gradient of KOAc, pH 8, was used for semipreparative HPAEC-PAD purification of oligogalacturonides. It should be noted that the resolution of oligogalacturonides is improved when NaOAc rather than KOAc is used as the eluant. Thus, NaOAc is the preferred eluant for analytical HPAEC-PAD.

The oligogalacturonides eluting from the semipreparative CarboPac column were detected by PAD and collected manually. Since no postcolumn alkali was added, the pH of the eluant (pH 8) was below that required for an optimal PAD response but nevertheless allowed for the detection of the oligogalacturonides. The oligogalacturonide fractions purified by semipreparative HPAEC-PAD were desalted by dialysis [2000 molecular weight cut off ($Mw_{co}$)], concentrated to 2 mL, and stored frozen.

Characterization of the tridecagalacturonide purified by semipreparative HPAEC-PAD. A portion of each semipreparative HPAEC-PAD-purified oligogalacturonide fraction was analyzed by HPAEC-PAD. In each case the fraction eluted as a single symmetrical peak with no other detectable components. The tridecagalacturonide, which is in the middle of the size range of the bioactive oligogalacturonides, was selected for structural and chemical characterization.

The $^1$H NMR spectrum of the tridecagalacturonide fraction contained signals (broad singlet) for anomeric protons at δ 5.08 that were assigned to (1→4)-linked α-D-galactosyluronic acid residues (Tjan et al., 1974; Ló and van Halbeek). Signals for anomeric protons at δ 5.30 and 4.60 were assigned to H-1α and H-1β, respectively, of the reducing galactosyluronic acid residue (Tjan et al., 1974; Ló and van Halbeek). Broad signals at δ 3.74, 4.00, 4.42, and 4.74 were assigned to H-2, H-3, H4, and H-5, respectively, of 4-linked galactosyluronic acid residues (Tjan et al., 1974; Ló and van Halbeek).

Negative-ion FABMS analysis of the tridecagalacturonide fraction gave an ion at m/z 2305 corresponding to [M−H]$^-$ of an oligogalacturonide containing 12 hexosyluronic acid residues and a single hexuronic acid. No other ions were detected.

The glycosyl-residue compositions of the tridecagalacturonide fraction, the NaOAc-ethanol-precipitated EPG digest of PGA, and PGA were determined by GLC and GLC-MS (EI and CI modes) analyses of their constituent trimethylsilyl-methyl ester-methyl glycoside derivatives. Galacturonic acid was the only sugar detected in the purified tridecagalacturonide. In contrast, the NaOAc-ethanol-precipitated material contained galacturonic acid and galactaric acid, arabinose, and xylose in the ratios of 1:0.03:0.02:0.005:0.006.

The combined evidence of spectroscopic data and chemical analyses indicates that the semipreparative HPAEC-PAD purified fraction contains only a homogeneous tridecagalacturonide.

Biological activity of the apparently homogeneous oligogalacturonides. The HPAEC-PAD-purified oligogalacturonides (dp between 10 and 15) each elicited phytoalexin synthesis in soybean cotyledons (Hahn et al., 1981; Nothnagel et al., 1983). The dodeca-, trideca-, and tetradecagalaturonides were the most active of the homogeneous oligogalacturonides. This result is consistent with previous studies (Hahn et al., 1981; Nothnagel et al., 1983) which established that a partially purified dodecagalacturonide was the most active elicitor of phytoalexin production in soybeans.

The semipreparative HPAEC-PAD purified dodeca-and trideca-galacturonides were both shown to promote flower formation and inhibit root formation in a tobacco thin-cell-layer morphogenesis assay. Both oligogalacturonide fractions demonstrated approximately equal activities, which is consistent with results obtained using partially purified dodeca- and trideca-galacturonides (Marfá et al., 1991).

The inventors have herein described a method for the preparation of milligram quantities of homogeneous bioactive oligogalacturonides. Approximately 14 mg of each homogeneous oligogalacturonide (dp between 10 and 15) can be prepared in three wk from 2 g of PGA. The amount of PGA digested with EPG can be increased to 20 g, and large quantities (~6 g) of material enriched in bioactive oligogalacturonides can be prepared by selective NaOAc-ethanol precipitation. In the inventors' experience, it is possible to scale up the Q-Sepharose chromatography step to fractionate 900 mg of NaOAc-ethanol precipitate on a 400 mL bed volume column without affecting the resolution. The low loading capacity (~6 mg) of the semipreparative CarboPac PA-1 column limits the amounts of homogeneous oligogalacturonides that can be prepared, although each chromatographic run is complete in 1 h.

The main emphasis of this study was the development of a method for the purification of homogeneous bioactive oligogalacturonides. However, smaller fragments (dp<10) are fully resolved using Q-Sepharose chromatography. Thus, relatively pure (~95% purity) oligogalacturonides (dp>9) can be obtained in large quantities (50–100 mg) without using the semi-preparative CarboPac column.

The purification of larger oligogalacturonides (dp>16) presents some major difficulties, since the solubility of oligogalacturonides decreases as their dp increases. The larger oligogalacturonides tend to precipitate on, and irreversibly bind to, anion-exchange media in the presence of high concentrations of salt. The inventors have found that the top 5 cm of the Q-Sepharose gel must be replaced after four or five runs to maintain the efficiency of the column. Further studies would be required to optimize the chromatographic conditions for the purification of oligogalacturonides with a dp>16.

Purification and Characterization of Biologically Active Tamarind Seed Oligosaccharides Xyloglucans (XGs) are a class of hemicellulosic polysaccharides that are found in noncovalent association with microcrystalline cellulose fibers in the cell walls of higher plants (McNeil et al., 1984; Bauer et al., 1973; Kooiman, 1961; York et al., 1988). The xyloglucan backbone consists of β-(1→4) linked D-Glcp residues that are substituted at C-6 with α-D-Xylp, β-D Galp-(1→2)-α-D-Xylp and α-L-Fucp-(1→2)-β-D-Galp-(1→2)-α-D-Xylp side chains (York et al., 1990). In addition, α-L-Ara f and β-D-Xylp substituents have been found at C-2 of some of the β-D Galp residues in the backbone of the xyloglucan produced by suspension-cultured *Acer pseudoplatanus* cells (Kiefer et al., 1990; Hisamatsu et al., 1992), and α-L-Ara f residues are found at C-2 of the α-D-Xyl residues in XGs produced by members of the Solanaceae (Ring et al., 1981; Mori et al., 1980). XGs are proposed to be major load-bearing structures in primary (growing) plant cell walls by virtue of their potential to crosslink cellulose fibers, and as such, are thought to play an important role in regulating plant cell-wall extension (Hayshai, 1989). Furthermore, very low concentration of xyloglucan oligosaccharides produced by the action of endo-(1→4)-β-glucanases can affect the growth of plant tissues (York et al., 1984; McDougall and Fry, 1988).

The combination of nuclear magnetic resonance spectroscopy (NMR) and fast-atom bombardment mass spectrometry (FABMS) provide a powerful method for determining the structures of oligosaccharides. The inventors have rigorously characterized the reduced forms (oligoglycosyl alditols) of many of the commonly occurring oligosaccharide subunits of xyloglucans (York et al., 1990; Kiefer et al., 1990; Hisamatsu et al., 1992). These analyses allowed the inventors to deduce a set of diagnostic correlations between the chemical shifts in the NMR spectrum and specific substructures in the oligoglycosyl alditols. The oligosaccharide subunits, obtained by high-resolution gel-permeation chromatography (Bio-Gel P-2) of the products formed upon treatment of xyloglucan polysaccharide with endo-(1→4)-

β-glucanase (*Trichoderma reesei*), are reduced with sodium borohydride and characterized spectroscopically. Various types of high-performance liquid chromatography (HPLC) are used to separate oligosaccharides that are not resolved, due to their similar size, by gel-permeation chromatography. The inventors have previously proposed (York et al., 1990) structures for two isomeric octasaccharides (Glc$_4$Xyl$_3$Gal) that are difficult to separate by HPLC, and which were therefore characterized as a mixture. The inventors now report that treatment of the oligosaccharide subunits from tamarind seed amyloid with a D-galactosidase from *Aspergillus niger* results in the selective hydrolysis of the β-D-Galp residues attached to the central xylosyl residue in one of these oligosaccharides. The selectivity of this enzyme made it possible to prepare large quantities of one of the isomeric octasaccharides, which the inventors have chemically reduced and characterized. The β-galactosidase-susceptible octasaccharide was also isolated, albeit in smaller quantities, by high pH anion-exchange chromatography (HPAE) of endo-(1→4)-β-glucanase glucanase-treated rapeseed xyloglucan. The $^1$H and $^{13}$C NMR spectra of the reduced octacaccharide isomers and a reduced pentasaccharide (Glc$_3$Xyl$_2$) were assigned. Additional correlations between the chemical shifts of certain resonances and the identity and distribution of side chains in xyloglucan oligoglycosyl alditols were deduced on this basis.

The correlations that the inventors have deduced between xyloglucan oligoglycosyl alditol structures and features in their NMR spectra make it possible to quickly and accurately determine considerable information about the structures of xyloglucans by inspection of their one-dimensional $^1$H NMR spectra (York et al., 1990; Hisamatsu et al., 1992). In applying these correlations the inventors have observed phenomena that, if not accounted for, could lead to incorrect conclusions about the structures of oligoglycosyl alditols being analyzed. These phenomena include the temperature dependence of the chemical shifts of certain resonances and the strong tendency of galactose-containing xyloglucan oligosaccharides to form borate complexes. Specific examples and general approaches to control these phenomena are presented.

Enzyme treatment of tamarind xyloglucan. Tamarind xyloglucan was digested with an endo-(1→4)-β-glucanase from *Trichioderma reesei* and separated into molecular size classes by Bio-Gel P-2 chromatography. Oligoglycosyl alditols were prepared by borohydride reduction of the nonasaccharide, octasaccharide, and heptasaccharide fractions and analyzed by $^1$H NMR spectroscopy. The $^1$H NMR spectrum of the oligoglycosyl alditols prepared by reduction of the octasaccharide-containing fractions 90–93 clearly shows the presence of more than one component. Structures 1–4 were proposed (York et al., 1990) to be the four most abundant endo-(1→4)-β-glucanase digestion products of tamarind xyloglucan. However, analysis of structures 2 and 3 had been based on the spectra of mixtures similar to the octasaccharide fraction described above, and, therefore, their structures were not unambiguously assigned.

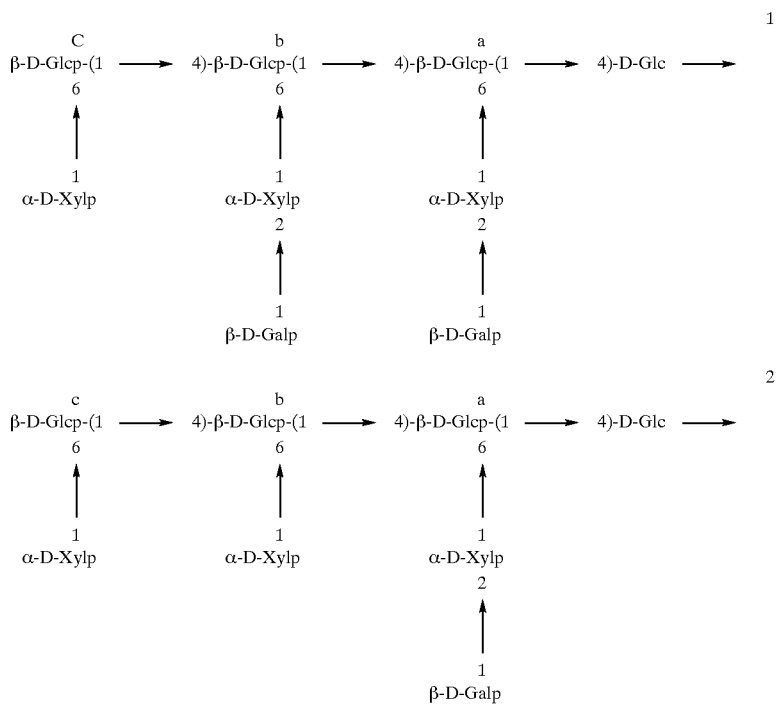

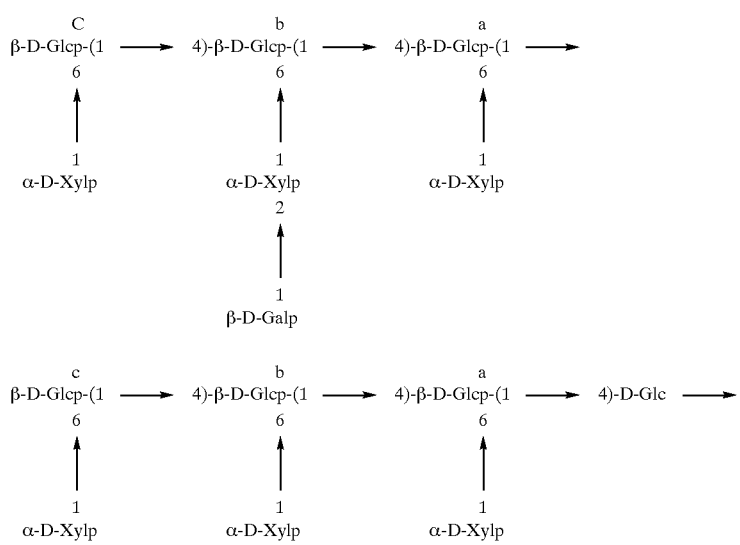

A mixture of the four oligosaccharides obtained by endo-(1→4)-β-glucanase treatment of tamarind xyloglucan was treated with a commercial preparation of a β-galactosidase secreted by *Aspergillus niger* and the products were separated by Bio-Gel P-2 chromatography. β-Galactosidase treatment resulted in the conversion of the bulk of nonasaccharide 1 (peak IX) to an octasaccharide that was the most abundant product recovered (peak VIII). The octasaccharide fraction was reduced with borohydride and analyzed by $^1$H NMR spectroscopy. It is evident from the $^1$H NMR spectrum that only one of the two isomeric octasaccharides survived the β-galactosidase treatment. The selectivity of the β-D-galactosidase for the β-D-Galp residues attached to C-2 of the central α-D-Xyl residue had resulted in the conversion of nonasaccharide 1 to octasaccharide 2 and the conversion of octasaccharide 3 to heptasaccharide 4 (peak VII). The recovery of large quantities of pure 2 allowed its structure to be unambiguously determined and the $^1$H and $^{13}$C NMR spectra of its corresponding oligoglycosyl alditol 2r to be fully assigned (see below).

A contaminating hydrolase activity present in the commercial β-galactosidase preparation partially degraded some of the oligosaccharides in the tamarind oligosaccharide mixture, leading to the formation of small (dp<7), late-eluting oligosaccharides. $^1$H NMR and FABMS analysis of the oligoglycaosyl alditols prepared by borohydride reduction of these oligosaccharides indicated that a contaminating hydrolase activity released the disaccharide isoprimeverose [α-D Xylp-(1→6)-D-Glc] from the nonreducing end of some of the oligosaccharides in the mixture. This analysis (See below) established that fractions 136–141 (peak I) contained only galactose released from 1 and 3 by β-galactosidase, while fractions 128–130 (peak 11) contained only isoprimeverose. Fractions 106–110 (peak V) contained only pentasaccharide 5, formed by the release of isoprimeverose from 4 or release of galactose from 6. P-2 fractions 100–104 (peak VI) contained hexasaccharide 6, formed primarily by the release of isoprimeverose from 2 (and perhaps to some extent by release of galactose from a short-lived intermediate Glc$_3$Xyl$_2$Gal$_2$, not detected in the mixture). Peak III and the barely detectable peak IV were not analyzed.

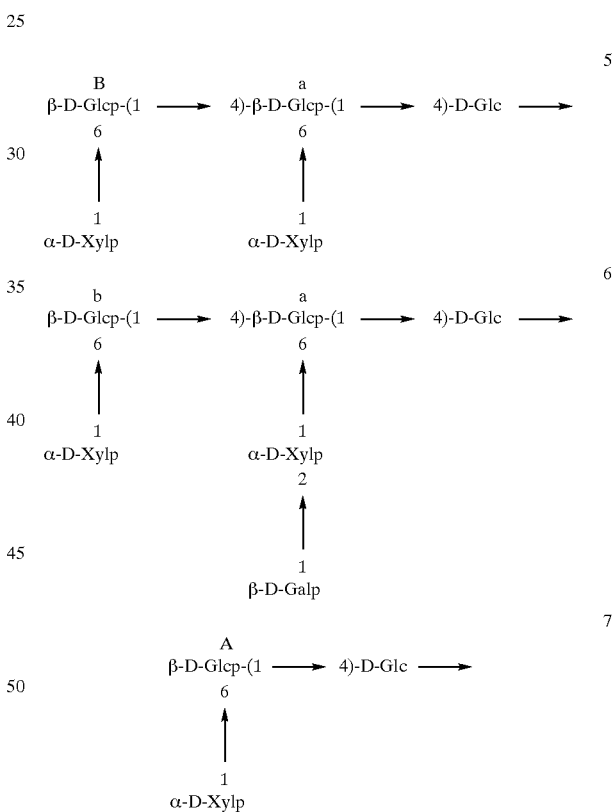

A glucosidase that releases isoprimeverose from the non-reducing end of xyloglucan oligosaccharides had previously been isolated from *Aspergillus oryzae* (Kato et al., 1985) and so its presence in the *Aspergillus niger* preparation was not surprising. Although the isoprimeverose-releasing enzyme represents only a small fraction of the total glycosidase content of the enzyme preparation, its effects were observed because xyloglucan oligosaccharides 1–4 are its preferred substrates, while these same oligosaccharides (especially 2) are quite poor substrates for the β-galactosidase. The xyloglucan oligosaccharides were treated with sufficient β-galactosidase (1.0 unit, as defined by the supplier, for 96 h) to hydrolyze more than 5000 μmol of the β-D-Galp residues in a preferred substrate, such as o-nitrophenyl β-D-galactoside. Nevertheless, only about half of the 215 μmol of β-D-Galp residues in the xyloglucan oligosaccharide mixture were hydrolyzed by the enzyme. The inventors estimate that ~30 μmol of isoprimeverose were released, corresponding to 0.005 units of the contaminating glucosidase.

Isolation of oligoglycosyl alditol 3r from rapeseed xyloglucan. Xyloglucan was extracted (York et al., 1990) from defatted rapeseed hulls and treated with endo-(1→4)-β-glucanase. The enzyme-digestion products included the two isomeric octasaccharides 2 and 3, but in a different ratio than was obtained from tamarind seed xyloglucan (York et al., 1990). A mixture of 2 and 3, prepared by Bio-Gel P-2 chromatography of the endo(1→4)-β-glucanase digestion products of rapeseed XG, was reduced with borohydride to oligoglycosyl alditols (2r and 3r), which were separated by HPAE chromatography with pulsed amperometric detection (PAD). The most abundant oligoglycosyl alditol in the sample, constituting ~75% of the rapeseed octasaccharide fraction, was eluted at 7.8 min. Its structure was established as 3r by the spectroscopic methods described below. The identity of the minor component (25% of the 1 sample, eluted at 9.4 min) was established as 2r by comparison of its chromatographic and spectroscopic signature to that of authentic 2r (obtained from tamarind, XG by sequential endo-(1→4)-β-glucanase and β-galactosidase treatment, see above). A mixture of oligoglycosyl alditols 2r and 3r was also prepared by reduction of the tamarind xyloglucan octasaccharide fraction and separated by HPAE chromatography. This analysis confirmed that 2r rather than 3r is the most abundant oligoglycosyl alditol in the reduced tamarind octasaccharide fraction, accounting for 75% of the sample.

High pH union-exchange chromatography of oliogosaccharides 2 and 3. Native (reducing) octasaccharides 2 and 3 have been separated by HPAE (McDougall and Fry, 1988), but their elution order was not unambiguously determined due to the difficulty in differentiating between the two closely related structures. The Bio-Gel P-2 octasaccharide fractions from both rapeseed xyloglucan and tamarind seed xyloglucan (no β-galactosidase treatment) were therefore subjected to analytical-scale HPAE chromatography without prior borohydride reduction. The relative amounts of 2 and 3 in these mixtures was established by peak integration and spectroscopic analysis of the HPAE-purified reduced forms 2r and 3r (see above). The HPAE elution order of the reducing oligosaccharides, 3 ($t_R$=15.9 min) followed by 2 ($t_R$=16.8 min), was thus determined on the basis of peak-area ratios for the two mixtures. The retention times of the reducing oligosaccharides were significantly longer than those of oligoglycosyl alditols, as expected (Lee, 1990), due to the greater acidity of the reducing glycosidic hydroxyl protons as compared to the alditol hydroxyl protons. The tendency of the glycosidic hydroxyl proton to ionize results in a higher average charge density (and stronger ionic binding to the matrix) for reducing oligosaccharides than for oligoglycosyl alditols.

Structural analysis of XG oligosaccharides. Oligosaccharides 1 to 6 were reduced with borohydride to the corresponding oligoglycosyl alditols 1r to 6r) and analyzed by $^1$H NMR spectroscopy and FABMS. All of the oligosaccharides except 3 were obtained by sequential endo-(1→4)-β-glucanase and β-d-galactosidase treatment of tamarind xyloglucan followed by P-2 chromatography. The major components of the nonasaccharide (peak IX), heptasaccharide (peak VII), disaccharide (peak II), and monosaccharide (peak I) fractions from the P-2 column were established as 1, 4, isoprimeverose and galactose, respectively, by comparing the $^1$H NMR and FABMS spectra of their borohydride-reduced forms to those of authentic standards (York et al., 1990). The octasaccharide (peak VIII), hexasaccharide (peak VI), and pentasaccharide (peak V) fractions obtained by this method contained oligosaccharides which were further analyzed after their conversion to oligoglycosyl alditols by borohydride reduction. In the description of this analysis (see below), the inventors use an abbreviated nomenclature (York et al., 1990, Hisamatsu et al., 1992) for substructures of the xyloglucan oligoglycosyl alditols. Glycosyl residues of the oligoglycosyl alditols are labeled with a superscript a, b, or c, depending on the proximity to the alditol moiety. Thus, backbone residues in the oligoglycosyl alditols are designated $Glc^c→Glc^b→Glc^a→Glcol$. The position of a side chain residue is indicated by the superscript character of the backbone residue to which the side chain is attached. For example, the galactosyl in 3r is designated $Gal^b$ as it terminates the side chain attached to $Glc^b$.

The $^1$H and $^{13}$C NMR spectra of oligoglycosyl alditols 2r, 3r, and 5r were fully assigned by two-dimensional techniques, and the $^1$H NMR spectra of 6r was partially assigned. Homonuclear COSY (Rance et al., 1983) and TOCSY (ax and Davis, 1985) spectra of the compounds were recorded, and proto resonances were assigned by virtue of their scalar-coupling patterns and connectivity, and by comparison to the previously assigned spectra of related oligoglycosyl alditols (York et al., 1990). The observed homonuclear scalar coupling constants were completely consistent with those of an related xyloglucan oligoglycosyl alditols and with the assignments presented herein. One-bond heteronuclear scalar connectivities were visualized by single-quantum coherence spectroscopy (HSQC) (Bodenhausen and Ruben, 1980; Otting and Wüthrich, 1988) or by two-dimensional inverse DEPT (Bendall et al., 1983). Examination of the HSQC or inverse DEPT spectra allowed nearly all of the $^{13}$C resonances of 2r, 3r, and 5r to be assigned. In addition, strongly coupled $^1$H systems (such as those for the alditol moieties) that could not be assigned by the homonuclear techniques were assigned on the basis of heteronuclear connectivities detected by HSQC. Correlations between the chemical shifts of anomeric proton resonances and specific oligoglycosyl alditol substructures are described below. Diagnostic signals (i.e., crosspeaks) involving nonanomeric resonances were also observed in the two-dimensional spectra and were correlated with specific structural features of oligoglycosyl alditols, but are not discussed due to space limitations.

Structures of the reduced octasacchayides. The inventors have described (York et al., 1990; Hisamatsu et al., 1992) many correlations between the chemical shifts of certain signals in the $^1$H NM spectra of xyloglucan oligoglycosyl alditols and specific details of their chemical structures. Most of these correlations were firmly established on the basis of thorough analysis of highly purified oligoglycosyl alditols. However, the analysis (York et al., 1990) of 2r and 3r had been performed on mixtures of two components. These analyses indicated that H-1 resonance (δ~5.16) of a $Xyl^a$ residue substituted at C-2 with a terminal β-Galp residue is slightly upfield of the H-1 resonance (δ~5.17) of a $Xyl^b$ substituted at C-2 with terminal β-Galp. The $^1$H NMR spectrum of the highly purified, borohydride-reduced β-galactosidase-resistant octasaccharide from tamarind includes α-anomeric proton resonance at δ 6.163 suggesting that its terminal galactosyl residue is attached to $Xyl^a$. The $^1$H NMR spectrum of the oligoglycosyl alditol prepared by HPAE chromatography ($t_R$=7.8 min, see above) of the reduced rapeseed octasaccharide fraction includes a signal at δ 5.175 suggesting that its terminal galactosyl residue is attached to $Xyl^b$. The glycosyl sequence of these oligoglycosyl alditols, and thus the validity of the correlations upon which these structural assignments were based, has now been unambiguously confirmed by FABMS (see below).

Negative-ion FABMS of the purified borohydride-reduced octasaccharides indicated a molecular weight of 1226 (i.e., $GalGlc_3Xyl_xGlcol$) for both samples. Alditol-end fragment ions (York et al., 1990) at m/z 637 (GalXylGlcGlcol) and m/z 931 ($GalXyl_2Glc_2Glcol$) in the spectrum of the reduced, β-galactosidase-resistant tamarind octasaccharide indicated that at terminal Gal residue was attached to $Xyl^a$ as in structure 2r. Conversely, alditol-end fragment ions at m/z 475 (XylGlcGlcol) and m/z 931 ($GalXyl_2Glc_2Glcol$) in the spectrum of the reduced rapeseed octasaccharide indicated that the terminal β-Gal residue was attached to $Xyl^b$ as in structure 3r.

Complementary sequence information was obtained by positive-mode FABMS of the per-O-acetylated oligoglycosyl alditols, which indicated a molecular weight of 2234 for both samples, consistent with the composition $GalXyl_3Glc_3Glcol$. The positive-ion spectrum of the reduced per-O-acetylated, β-galactosidase-resistant octasaccharide from tamarind xyloglucan included high abundance, nonreducing end fragment ions (York et al., 1990) at m/z 547 (XylGlc and GalXyl) and m/z 1051 ($Xyl_2Glc_2$). Fragment ions at m/z 1339 were present in very low abundance in this spectrum, and could be attributed to a low-probability, double-cleavage event (York et al., 1990) leading to an ion with the composition $Glc_3Xyl_2$. These features indicated that the β-Gal residue was not attached to $Xyl^b$ or $Xyl^c$ in the β-galactosidase-resistant octasaccharide. The fragment ion observed at m/z 1843 ($GalXyl_3Glc_3$) is consistent with attachment of the terminal-Gal residue to $Xyl^a$ (structure 2r) in the β-galactosidase-resistant octasaccharide. Conversely, the high abundance of fragment ions at m/z 547 (XylGlc and GalXyl) and m/z 1339 ($GalXyl_2Glc_2$) and low abundance of ions at m/z 835 (GalXylGlc) and m/z 1051 in the positive-ion spectrum of the reduced, per-O-acetylated rapeseed octasaccharide indicated that the β-Gal residue was attached to $Xyl^b$ in this molecule (structure 3r).

Structures of the reduced penta- and hexa-saccharides. The structure, borohydride-reduced pentasaccharide from tamarind XG treated with endo-(1→4)-β-glucanase and galactosidase, was assigned as 5r on the basis of the chemical shifts of diagnostic resonances (York et al., 1990) $^1$H NMR spectrum. Only two α-anomeric signals wee observed in the $^1$H NMR spectrum of reduced fraction V, having chemical shifts corresponding (York et al., 1990) to H-1 of a terminal α-Xylp residue (i.e., $Xyl^b$, δ 4.942) attached to C-6 of a unbranched β-Glcp residue and H-1 of a terminal α-Xylp residue (i.e., $Xyl^a$, δ 4.956) attached to a -(4→6)-linked β-Glcp residue. The signal at δ 4.634 corresponds (York et al., 1990) to a H-1 of a (4→6)-linked β-Glcp residue ($Glc^a$) attached directly to the alditol, and the resonance at δ 4.567 is due (York et al., 1990) to H-1 of another backbone β-Glcp residue ($Glc^b$). The four glycosyl residues (two α and two β) in the chemical environments that were deduced from the $^1$H NMR spectrum can combine with a glucitol residue in only one arrangement (structure 5r), which was confirmed by FABMS (see below).

Structure 6r was assigned to the main component of the borohydride-reduced P-2 fraction VI. The $^1$H NMR spectrum of this sample contains a signal (δ 4.941) corresponding (York et al., 1990) to H-1 of a terminal α-Xylp residue ($Xyl^b$) linked to C-6 of an unbranched β-Glcp residue. The other a-anomeric signal (δ 5.170) in the spectrum corresponds (York et al., 1990) to H-1 of an α-Xylp having a β-Galp substituent at C-2. The chemical shift of this resonance is approximately midway between that of H-1 of the 2-linked α-Xylp residue in 2r (δ 5.163) and H-1 of the 2-linked α-Xlyp residue in 3r (δ 5.175), which is consistent with unique position of the β-Galp (1→2)-α-Xylp side chain of 6r. This side chain is linked to C-6 of a β-Glcp residue with an alditol aglycon (as in 2r) and an unbranched, 6-linked β-Glcp substituent at C-4 (as in 3r). Three β-anomeric signals (δ 4.542, 4.556, and 4.621) in the $^1$H NMR spectrum of fraction VI correspond (York et al., 1990) to a (4→6) linked β-Glcp residue ($Glc^a$) glycosidically linked to the alditol, a terminal β-Galp residue, and another backbone β-Glcp residue, respectively. Again, these five glycosyl residues in the chemical environments that are indicated by the chemical shifts of their anomeric protons can only be combined with a glucitol residue in one arrangement (structure 6r), which was confirmed by FABMS.

The glycosyl sequences the oligoglycosyl alditols (compounds 5r and 6r) formed by borohydride-reduction of P-2 fractions VI and VI, respectively, were confirmed by FABMS. Their molecular weights were established by negative-ion FABMS as 770 ($Xyl_2Glc_2Glcol$) for 5r and 932 ($GalXyl_2Glc_2Glcol$) for 6r. The high abundance of the m/z 637 ion (GalXylGlcGlcol) and low abundance of the m/z 475 ion (XylGlcGlcol) in the negative-ion FAB mass spectrum of 6r indicated that the terminal β-Galp residue in 6r was attached to $Xyl^a$. The negative-ion FAB mass spectrum of 5r included abundant ions at both m/z 475 (XylGlcGlcol) and m/z 637 ($XylGlc_2Glcol$). Complementary glycosyl sequence information for these oligoglycosyl alditols was obtained by positive-ion FABMS of their per-O-acetylated derivatives, which indicated molecular weights of 1442 ($Xyl_2Glc_2Glcol$) for 5r and 1730 ($GalXyl_2Glc_2Glcol$) for 6r. The high abundance of nonreducing end fragment ions at m/z 547 (XylGlc and GalXyl) 1339 ($GalXyl_2Glc_2$) and low abundance of ions at m/z 1051 ($Xyl_2Glc_2$) in the positive-ion FAB mass spectrum per-O-acetylated 6r confirmed that its galactosyl residue was attached to a side chain a. Abundant fragment ions at m/z 547 (XylGlc) and 1051 ($Xyl_2Glc_2$) in the positive-ion FAB mass spectrum per-O-acetylated 5r were consistent with its proposed structure.

The spectral data obtained in this study when combined with previously described data (York et al., 1990; Hisamatsu et al., 1992), allowed additional correlations between xyloglucan oligoglycosyl alditol structure and proton chemical shifts to be deduced. For example, the H-1 resonance of the (4→6)-linked O-$Glc^a$ is relatively easy to identify in the $^1$H NMR spectra of xyloglucan oligoglycosyl alditols, especially if COSY or TOCSY data are available. The chemical shift of this resonance is shifted upfield (−0.005 to −0.013 ppm) by substitution of α-$Xyl^a$ with a β-Gal residue at C-2 but downfield (0.009 to 0.015 ppm) by substitution of α-$Xyl^b$ with a β-Gal residue at C-2. This situation is typical for the β-anomeric resonances of xyloglucan oligoglycosyl alditols, which often exhibit more complex dependence on the nature and location of side-chain structures than do the α-anomeric resonances (York et al., 1990).

Effect of residual borate on NMR spectra. Reduction of xyloglucan oligosaccharides with borohydride eliminates the complicating effects of anomeric equilibria at the reducing end and therefore results in simplification of their $^1$H and $^{13}$C NMR spectra (York et al., 1990). In addition, the FAB mass spectra of underivatized and per-O-acetylated xyloglucan oligoglycosyl alditols are significantly easier to interpret than those of the unreduced oligosaccharides (York et al., 1990; Kiefer et al., 1990). However traces of borate not completely removed during cleanup of the reduced samples form complexes with the oligoglycosyl alditols, leading to anomalies in the NMR spectra. Borate appears to selectively interact with side chains containing galactosyl (and fucosyl) residues (see below) producing chemical shift effects in the chain to which borate is esterified.

Specific chemical shift effects of the interaction of oligoglycosyl alditol 2r with borate were examined by recording $^1$H NMR spectra of highly purified 2r in the presence of various additives. The spectrum recorded in the absence of additives included signals at δ 5.5164 (H-1 of 2-linked αXyl$^a$) and δ 4.622 (H-1 of β-Glc$^a$). Addition of ~2 L (35 μmol) of acetic acid-d₁ brought the pD to ~4, but had no effect on the carbohydrate signals in the spectrum. Subsequent addition of 25 μmol of $Na_2CO_3$ and 20 μequiv of borate (5 μmol of $Na_2B_4O_7$) brought the pD to 7.5, and resulted in a broadening and splitting of the H-1 resonance of the α-Xyl$^a$ residue and a broadening of the H-1 resonance of β-Glc$^a$. Further adjustment of the pD to ~9 with $Na_2CO_3$ resulted in a single (broad) signal at δ 5.174 for α-Xyl$^a$H-1, thus appearing to complete the transformation of the magnetic environment for this nucleus that was observed at pD 7. This result is consistent with a pD-dependent shift (Kennedy and How, 1973) in the equilibrium concentration of the free and borate-complexed forms of 2r. In addition, the β-Glc$^a$ resonance at δ 4.622 was completely missing at pD 9 as a result of extreme line broadening and/or chemical shift effects. Finally, adjustment of pD to ~5 by addition of acetic acid-d₁ caused the borate complexes to dissociate and the original appearance of the spectrum to be reestablished.

The chemical shifts of signals in the a-anomeric region (4.9<δ<5.3) of the spectrum of 2r in the presence of alkaline borate are nearly identical to those in the spectrum of purified, borate-free 3r. Although the two can be distinguished on the basis of signals in the β-anomeric region (4.4<δ<4.7), the complete exclusion of borate-carbohydrate complexes from the sample is generally required for unambiguous results. Experiments involving the formation of borate complexes with mixtures of 2r and 3r (obtained from rapeseed and tamarind xyloglucan) were performed in order to demonstrate that the correlations that the inventors have observed between the chemical shifts of $^1$H NMR resonances and substructures of these oligoglycosyl alditols were not based on artifacts that resulted from the presence of traces of borate. These experiments showed that, under conditions where borate complexes did not form (i.e., no borate and/or low pD), the spectra contained the diagnostic signals for both components in the expected ratios, and that formation of borate complexes resulted in chemical shift and line-broadening phenomena similar to those described above for homogeneous 2r.

Borate can be removed by passing the oligoglycosyl alditols through a mixed-bed ion-exchange resin, as previously suggested (York et al., 1990), but the anion-exchange phase of these resins tend to bind carbohydrate, resulting in unacceptably low recoveries for samples that contain only small amounts of material. Samples dissolved in $D_2O$ can be titrated to pD<6 with acetic acid-d₁ in order to prevent the formation of borate complexes (see above). Alternatively, the sample can be passed through a strong cation-exchange resin in the H$^+$ form, followed by repeated additions and evaporations of methanol to remove borate as its trimethyl ester. Care must be taken, however, to insure that the sample does not contain the salts of nonvolatile strong acids, because the acidic residue remaining after the cation-exchange will destroy the oligoglycosyl alditol. Sulfuric acid, which is formed from sulfate salts commonly found in enzyme preparations used to released the oligosaccharides from the polymer, is particularly destructive. Sulfate salts are often coeluted with oligosaccharides during BioGel P-2 chromatography, in spite of their significant difference in size, due to processes such as solvation of ions and ionic interactions with the matrix.

Effects of temperature variation. Certain proton spectra of $^1$H NMR spectra of xyloglucan oligoglycosyl alditols exhibit significant temperature-dependent chemical shift effects, and so comparative analysis of these spectra requires careful temperature control. For example, the chemical shift of H-1 of the (2-linked) αXyl$^a$ in the $^1$H NMR spectrum of 2r varies from δ 5.167 to 5.160 in the temperature range 296 to 302 K. Structure-dependent chemical shift effects were unambiguously distinguished from temperature-dependent chemical shift effects by recording spectra after adjusting the sample temperature to a point slightly above the ambient room temperature such that the chemical shift of the (highly temperature-dependent) HDO resonance was 4.75±0.01 ppm, relative to internal acetone at 2.225 ppm. This corresponded to a setting of 298 to 300 K on the temperature control unit of the Bruker AM 500 spectrometer.

Protocol for Testing Materials for Protection of Delayed Type Hypersensitivity Immune Response Against Suppression by Ultraviolet Radiation C3H female mice were anesthetized and their shaved dorsal skin was exposed to 5–10 kJ/m$^2$ Ultraviolet B (UVB) radiation. Immediately after exposure an unbuffered solution of Aloe, oligogalacturonides, or tamarind xyloglucan reconstituted in water was applied to the irradiated dorsal skin. After a 3 day recovery period, the mice were immunized by a subcutaneous injection in their flank with formalin-fixed *Candida albicans* yeast cells (2×10$^7$ per mouse). Ten days later, a period of time sufficient for the immune response to develop, delayed type hypersensitivity was measured. This was done by injecting the animals in their hind footpads with a commercially available, soluble preparation of Candida antigen (50 microliters per footpad). The next day, the footpad swelling was measured. Controls included: (i) animals that received no UVB injury or sensitization but were challenged in their hind footpads with the soluble antigen (unsensitized negative controls), (ii) animals which received no UVB injury or treatment with the carbohydrates but which were immunized with the Candida cells, (Sensitization Control), (iii) animals which were not UVB-irradiated but received the Aloe, oligogalacturonides, or tamarind and were immunized with the Candida cells (Matching Positive Controls), and (iv) animals that were UVB irradiated and immunized with the Candida cells but were not treated with Aloe, oligogalacturnoides or tamarind xyloglucans (Fully Suppressed No Rx Control). The data was recorded as footpad swelling as the average of both hind footpads. All studies were conducted with groups of 5 mice.

Figure 4:
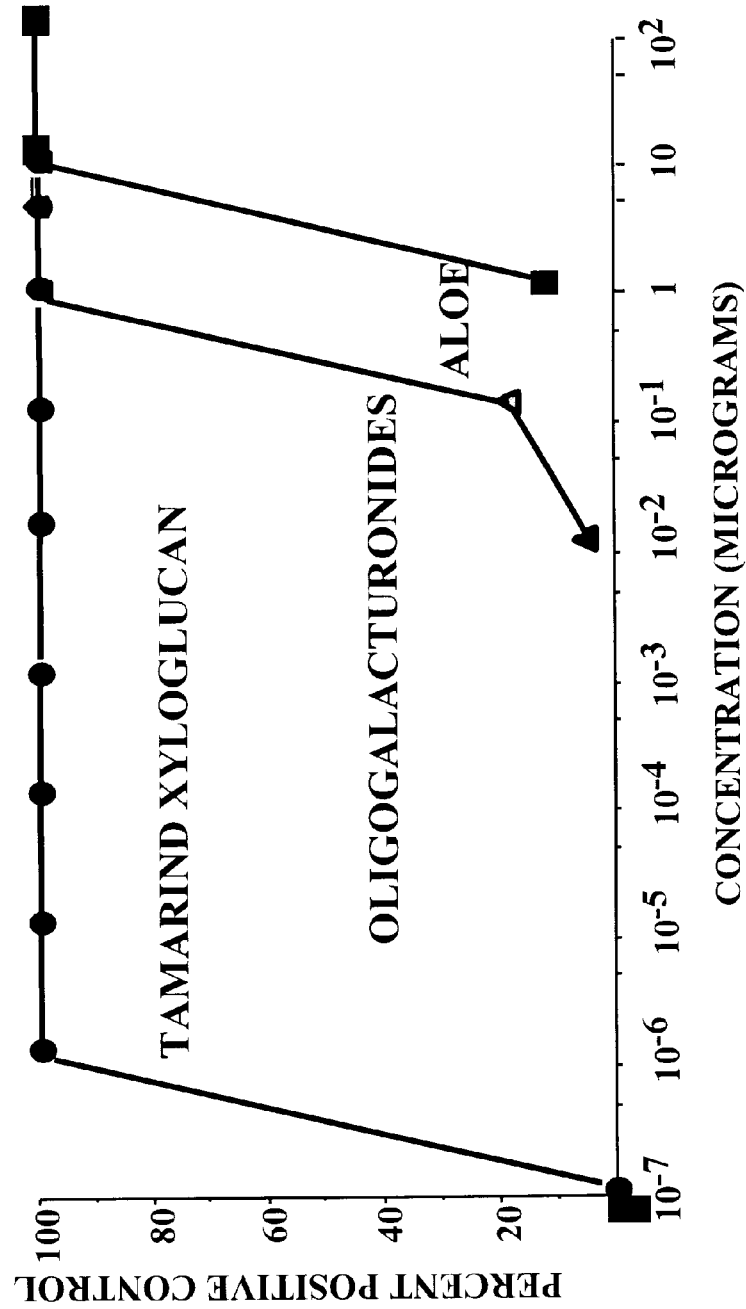
FIG. 4 shows DTH data presented as percent positive control. Complete suppression of the immune response is expressed as 0% and complete restoration of the response is expressed as 100%.

In order to more clearly discern therapeutic effects above and beyond the usual variation that is observed from study to study, the data was transformed to normalize values as the inventors have previously published (Byeon et al., 1998). The Matching Positive Control was normalized for each study to 100% and the fully Suppressed No Rx Control was normalized to 0% for each study. Therefore, the data in FIG. 4 are presented as percent positive control. Complete suppression of the immune response is expressed as 0% and complete restoration of the response is expressed as 100%.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Aloe barbadensis Materials

The *Aloe barbadensis* gel preparations used were "Aloe Research Foundation Standard Gel Samples" prepared for the Aloe Research Foundation by AloeCorp (Harlingen, Tex.), as previously described (Strickland et al, 1994). These "Process A" materials were from lots ARF'91A, ARF'94B, ARF'94G, and ARF'94K (Pelley et al, 1993). In general, the composition of matter of these lyophilized materials was 9.6% polysaccharides, 11% glucose, 27% divalent metal cations and multivalent organic acids, and less than 5% materials extractable with organic solvents. The remainder consisted of univalent metal cations, chloride, and univalent organic acids. At the time of lyophilization, the total bacterial content was always under 30,000 per ml of gel. Although this extract was prepared on an industrial scale using commercial equipment, it does not correspond to any commercial product.

An oligosaccharide-rich material was prepared from crude "Process A" gel by activation with cellulase followed by separation of small molecules from enzyme and polysaccharide by ultrafiltration. Frozen ARF 94K crude Aloe gel (2 liters, solids content 14 g) was thawed and 2.3 mg of crude commercial cellulase (Cellulase 4000, Valley Research, South Bend, Ind.) was added. The enzyme-Aloe mixture was ultrafilter fractionated by multiple cycles through a 5000 dalton cut-off polysulfone hollow fiber apparatus (2790 cm$^2$, A/G Technology, Needham, Mass.). Each cycle consisted of passing the material, at ambient temperature, through the ultrafilter at a pressure sufficient to produce diffusate at a rate of 2 liters per h. Retentate volume was kept constant by the addition of deionized water. As each 2 liter portion of diffusate was produced, it was removed and concentrated by lyophilization. Four cycles of enzymatic treatment-ultrafiltration were performed. The first diffusate yielded 60% of the total dialyzable mass, the second yielded 24%, and the third and fourth diffusates combined accounted for 12% of the total dialyzable mass.

More highly purified oligosaccharides were prepared by cleavage of purified Aloe polysaccharides with partially purified cellulase followed by separation of oligosaccharides from enzyme and polysaccharide by alcohol precipitation. Polysaccharide was purified from lyophilized "Process A" Aloe, lot ARF94K by modification of the method of Gowda using exhaustive dialysis followed by precipitation at 80% vol/vol with absolute ethanol at 4° C. (Gowda et al, 1979). This yielded (14.2% of mass) a polysaccharide of expected sugar composition (7% glucose, 85% mannose, 4% galactose), almost all of which was in excess of 2,000,000 Da molecular weight. Cellulase was purified from crude *T. reesei* concentrated culture supernatants (lot ZPED, obtained from Valley Research, South Bend, Ind.) by ethanol precipitation (50–80% fraction) and gel filtration upon Biogel P-200 (Bio-Rad, Richmond, Calif.). The protein concentration of the partially purified cellulase was determined by the Coomassie Blue dye binding assay (Bio-Rad, Richmond, Calif.). Oligosaccharide was produced by incubating 400 mg of purified polysaccharide with 12 μg of partially purified cellulase in 5 mM citrate buffer (pH 6) at ambient temperature for 2 h. This treatment reduced the viscosity of the solution by 50% but resulted in only a minor shift in the molecular weight distribution of the Aloe polysaccharides. Oligosaccharides were separated from precursor polysaccharide and enzyme by addition of absolute ethanol to 80% vol/vol and chilling to 4° C. The oligosaccharide containing supernatant was then separated from the precipitate (which contained the enzyme and polysaccharide) by centrifugation. Oligosaccharide, measured as hexose, constituted only 1.5% of the mass of the supernatant after stripping and lyophilization (the vast bulk of the supernatant consisting of the sodium citrate buffer). Oligosaccharides used for in vitro culture were diluted in serum-free minimal essential medium (MEM; Gibco, Grand Island, N.Y.) and filter sterilized through a 0.22 μm membrane.

EXAMPLE 2

Oligogalacturonide Materials

Polygalacturonic acid (Na$^+$ salt) was purchased from Sigma (St. Louis, Mo.) and used without further purification. SpectraPor-7 1000 and 2000 MW$_{co}$ tubing was purchased from Fisher Scientific. Dialysis was performed at 4° C. All buffers were prepared using ultra-pure water (Continental Ultrafiltration Water System, San Antonio, Tex.). All other materials were obtained from Sigma unless otherwise stated.

Treatment of polygalacturonic acid with a purified fungal α-(1→4)-endopolygalacturonase (EPG). A solution of polygalacturonic acid (2 g) in 20 mM NaOAc, pH 5.0 (100 mL), containing bovine serum albumin (1 mg) as a carrier protein, was treated for 8 h at 23° C. with α-(1→4)-endopolygalacturonase (15 units; 1 unit releases 1 mM reducing sugar per min at 24° C). The EPG had been purified to homogeneity from the culture medium of *Fusarium moniliforme* (Hahn et al.) (obtained from C. Bergmann of this laboratory). The enzymic reaction was terminated by autoclaving the solution for 15 min at 121° C. An aliquot (50 μL) of the enzymic digest was analyzed by HPAEC-PAD to determine the size distribution of oligogalacturonides.

Selective precipitation of oligogalacturonides with a dp>6 by treatment of EPG-digested PGA with EtOH and NaOAc. The partial EPG digest of PGA was adjusted to contain 0.5% galacturonic acid residues (w/v), 50 mM NaOAc, and 11% EtOH (v/v) by the sequential addition of water, solid NaOAc, and abs EtOH while stirring. The mixture was kept for 16 h at 4° C. The precipitate that formed was collected by centrifugation (30,000 g for 30 min at 4° C). The supernatant was decanted, dialyzed (1000 MW$_{co}$), concentrated to dryness, and the residue stored at −20° C. The pellet was washed with cold aq 50% EtOH (2×20 mL) and stored at −20° C. Aliquots of the EtOH-soluble and EtOH-precipitated material (100 μg each) in water (100 μL) were analyzed by HPAEC-PAD to determine the size distribution of the oligogalacturonides.

Q-Sepharose chromatography of the oligogalacturonides precipitated by EtOH and NaOAc. A solution of the NaOAc-EtOH-precipitated oligogalacturonides (450 mg galacturonic acid equivalents) in 50 mM ammonium formate (50 mL) was adjusted to pH 6.5 with 10 mM ammonium hydroxide. Ammonium formate (1 M) was added until the conductivity of the solution was equal to that of 300 mM ammonium formate. The mixture was loaded onto a Q-Sepharose column (2.2×50 cm) that had been equilibrated with 300 mM ammonium formate, pH 6.5. The oligogalacturonides were eluted by a two-stage concentration gradient of ammonium formate, pH 6.5, at a flow rate of 5 mL/min. During the first stage of the gradient, the ammonium formate concentration was increased from 300 to 420 mM over 120 min, and the eluant was discarded. The ammonium formate concentration was then raised to 470 mM over the next 400 min, and fractions (10 mL) collected. Aliquots (50 µL) of every second fraction were assayed colorimetrically (Blumenkrantz and Asboe-Hansen, 1973) for uronic acid. Fractions corresponding to uronic acid-containing peaks were pooled, dialyzed (2000 $MW_{co}$), and freeze dried. Aliquots (100 µg) of each of the pooled peaks were analyzed by HAEC-PAD to determine the dp of the major component and the degree of purity of the sample.

Semipreparative HPAEC-PAD purification of the oligogalacturonides isolated by NaOAc-EtOH precipitation and Q-Sepharose chromatography. Semipreparative HPAEC-PAD was performed with a Dionex metal-free BioLC interfaced to an Autolon series 400 data station. Portions (5 mg) of the pooled peaks of Q-Sepharose-resolved oligogalacturonides between dp 10 and 15 in water (500 µL) were separated on a semipreparative CarboPac PA-1 column (9×250 mm; Dionex, Sunnyvale, Calif.) and detected using a pulsed amperometric detector equipped with a gold working electrode (Dionex, Sunnyvale, Calif.). The electrochemical detector was operated in the pulsed amperometric mode (E1, 150 mV; E2, 700 mV; and E3, −300 mV; TI, 480 ms; T2, 120 ms; and T3, 360 ms) at 3 µA sensitivity. Eluants were filtered (0.2 µM Nylon 66 membranes; Rainin, Woburn, Mass.) and degassed with He using an eluant degas module (Dionex, Sunnyvale, Calif.). The column was eluted at 5 mL/min with a linear concentration gradient (550–675 m of KOAc, pH 8. No postcolumn NaOH was added in order to minimize base-catalyzed modification of the sample. The oligogalacturonides were collected manually while monitoring the PAD output. The resulting fractions were desalted by dialysis (2000 $MW_{co}$), concentrated to 2 mL, and stored at −20° C.

Analytical HPAEC-PAD of oligogalacturonides. Solutions of oligogalacturonides (100–500 µg) in water (250 µL) were separated on a CarboPac PA-1 column (4.6×250 mm) using a linear gradient from 400–800 mM NaOAc, pH 8, at 1 mL/min over 40 min. The column was re-equilibrated with 400 mM NaOAc for 15 min before loading the next sample. To facilitate the detection of carbohydrates and to minimize baseline drift, NaOH (400 mM) was added postcolumn at a flow rate of 0.5 mL/min using a pressurized reagent delivery system (Dionex, Sunnyvale, Calif.). The electrochemical detector was operated at 1000 nA sensitivity in the pulsed amperometric mode as described for semipreparative HPAEC-PAD. This procedure separates oligogalacturonides between dp 3 to 25.

Glycosyl-residue composition analysis. PGA and the oligogalacturonide-containing samples (100 µg) were separately treated with M HCl in MeOH (250 µL, 16 h at 80° C.). The resulting methyl ester-methyl glycosides were then trimethylsilylated and analyzed on an HP 5880A GC using a DB-1 30 m column with split injection (York et al., 1985). The peaks were identified by comparison of their retention times to those of standard monosaccharide derivatives and by GLC-MS (EI and CI modes; ammonium as the reagent gas) using an HP 5985 GLC-MS system.

Fast-atom-bombardment mass spectrometry (FABMS). FAB-mass spectra were recorded with a VG ZAB-SE mass spectrometer (VG Analytical, Altringham, UK) operating in the negative-ion mode with an accelerating voltage of 8 kV. The oligogalacturonides were converted to their ammonium salt forms using Chelex 100 ion-exchange resin (ammonium form; Bio-Rad, Richmond, Calif.). A portion (1 µL) of the ammonium-oligogalacturonate in water (10 mg/mL) was applied to a mixture of M HCl (0.5 µL) and thioglycerol (1 µL) on the probe tip of the mass spectrometer.

$^1$H NMR spectroscopy. $^1$H NMR spectrometry was performed with a Bruker AM 250 spectrometer. The oligogalacturonide samples were exchanged three times with $^2$H$_2$O (Aldrick, 99.96%) prior to $^1$H NMR spectroscopy. Chemical shifts are reported in δ-units (ppm) downfield from Me$_4$Si. HOD (δ 4.8) served as the internal reference.

EXAMPLE 3

Tamarind Seed Xyloglucan Oligosaccharides

*Xyloglucan oligosaccharides.* Tamarind seed xyloglucan (200 mg, prepared by EtOH precipitation as previously described (York et al., 1990)) was incubated (96 h, ambient temperature) in buffer (100 mL, 50 mM HOAc-NaOAc, pH 5.2) containing endo-(1→4) β-glucanase (20 units) from *Trichoderma reesei* (Megazyme Australia, Inc.). β-Galactosidase NC 3.2.1.23) from *Aspergillus niger* (Sigma Chemical Co., Cat. No. G 3522, 1 unit) was added to an aliquot consisting of 90% of the endo-(1→4)-β-glucanase (EC 3.2.1.4) digest which had been acidified (pH 4.5) with glacial HOAc, and the solution was incubated for 96 h. Enzymes and salts were removed from the two aliquots (±β-galactosidase) by passing the solutions through a column of Amberlite (MB-1 (10 and 2 mL, respectively). The eluates were lyophilized, dissolved in 2 mL of H$_2$O, and separated into size classes by high-resolution BioGel P-2 chromatography (FIG. 1), as had been described (York et al., 1990). Xyloglucan oligosaccharides were also prepared by endo-(1→4)-β-glucanase digestion of xyloglucan purified from rapeseed hulls (York et al., 1990).

Oligoglycosyl alditols. Oligosaccharides (0.5–3.0 mg) were reduced in aq NH$_4$OH (1M, 250 µL) containing NaBH$_4$ (10 mg/mL). The borohydride was quenched with glacial HOAc added dropwise until no further effervescence was observed, and the solution was passed through AG 50W-X4 (H$^+$, Bio-Rad) cation-exchange resin. The solvent was evaporated and borate was removed by repeated addition and evaporation of CH$_3$OH (1 mL aliquots).

High-pH anion-exchange chromatography (HPAE). Oligosaccharides or oligoglycosyl alditols were dissolved (1–10 µg/µL) in H$_2$O and injected (20 µL) onto a Dionex CarboPac PA1 column (4×250 mm) equilibrated in 100 mM NaOH, containing 50 mM NaOAc (solution A). Separation was accomplished by elution with solution A for 1 min, followed by a 20 min linear gradient elution starting with solution A and ending with 100 mM NaOH containing 100 mM NaOAc (solution B), and finally isocratic elution with solution B for 20 min. All steps were carried out at a flow rate of 1 mL/min with pulsed amperometric detection.

FAB-mass spectrometry. FAB-mass spectra were recorded with a VG Analytical ZAB-SE mass spectrometer operating at low resolution (1:1000) with an accelerating voltage of 8 kV. Underivatized oligoglycosyl alditols (1 µL of a ~10 µg/µL solution in H$_2$O) were mixed on the probe tip with 3-amino-1,2-propanediol (2 µL, Aldrich) for negative-ion FABMS. Oligoglycosyl alditols (100–500 µg) were per-O-acetylated with a mixture of trifluoroacetic anhydride and HOAc (Dell and Tiller, 1986), dissolved (10 µg/µL) in CH$_3$OH, and ~1 µL of this solution was mixed on the probe tip with thioglycerol (3-mercapto-1,2-propanediol, 2 µL, Aldrich) for positive-ion FABMS. The nominal masses reported herein were calculated from the observed monisotopic exact masses of resolved isotopomers or from the chemical masses of unresolved high-mass ion clusters using the CARBOMASS (York et al., 1988) software developed in this laboratory.

NMR Spectroscopy. Hydroxyl protons of the oligoglycosyl alditols were exchanged with deuterones, samples (0.5–5 mg) were dissolved in $D_2O$ (0.5 mL), and NMR spectra were recorded, at ~299 K (HDO line at δ 4.75±0.01 relative to internal acetone at δ 2.225), with a Bruker AM 500 NMR spectrometer, except for the two-dimensional spectra of 3r, which were recorded with a Bruker AMX 600 spectrometer. Double-quantum filtered {$^1H$, $^1H$} COSY (Rance et al., 1983) spectra and 2D $^1H$ TOCSY (Bax and Davis, 1985) (HOHAHA) spectra were obtained under previously described (York, et al., 1990) conditions.

{$^1H$, $^{13}C$} HSQC spectra were recorded using the pulse sequence of Bodenhausen and Ruben (1980) using composite 180° proton pulses (e.g., $90_x180_y90_x$) and two 3 ms spin-lock purge pulses (Otting and Wüthrich, 1988) to eliminate the resonances of protons attached to $^{12}C$. Typical aquisition parameters for {$^1H$, $^{13}C$} HSQC spectroscopy at 500 MHz included a spectral width of 1250 Hz (2.5 ppm) in 2048 data points for the $^1H$ dimension ($t_2$), a spectral width of 7200 Hz (57.25 ppm) in 128 data points, zero-filled to 512 data points for the $^{13}C$ dimension ($t_1$), and a relaxation delay of 1 sec between each of the 128 transients per to increment. $^{13}C$ Decoupling during signal aquisition was accomplished with the GARP pulse sequence (Shaka et al., 1985) (~4 watts power generated with the Bruker BFX-5 pulse amplifier).

{$^1H$, $^{13}C$}Inverse DEPT correlation spectroscopy was performed using a modification of the pulse sequence of Bendall et al. (1983) with proton presaturation via WALTZ-16 during the relaxtion delay. Chemical shift labeling in $t_1$ was accomplished by moving the first 90° $^{13}$Cpluse incrementally into the presaturation period, which was kept constant (2.0 s), and phase-sensitive sepctra were obtained by incrementing the phase of this pulse by 90° for each $t_1$ (i.e., a time proportional phase increment, TPPI (Marion and Wüthrich, 1983). Other parameters were comparable to those used for recording HSQC spectra, except that the data for the $^1H$ dimension consisted of 1024 data points. The pulse angle θ of the first proton pulse was set to 45°, giving all positive signals (Bendall et al., 1983). This approach has the advantage of permitting spectral editing based on the multiplicity of $^{13}C$-attached protons (Bendall et al., 1983) and provided high quality heteronuclear correlation spectra for 2r. Nevertheless, its lack of sensitivity relative to that of HSQC made it inappropriate for the other oligoglycosyl alditols, which were only available in small quantities. Proton pulses for the TOCSY, HSQC and inverse DEPT experiments were generated by the decoupler.

EXAMPLE 4

Treatment of Mice

Specific-pathogen-free female C3H/HeN Cr (MTV⁻) mice were obtained from the Animal Production Area of the Frederick Cancer Research Facility (Frederick, Md.) and were maintained in a pathogen-free barrier facility in accordance with the National Institutes of Health and the American Association for Assessment and Accreditation of Laboratory Animal Care International guidelines. The mice were housed in filter protected cages and provided with National Institutes of Health open formula mouse chow and sterile water ad libitum. All procedures were approved by the Institutional Animal Care and Use Committee. Each study was performed with aged matched mice that were 10–12 wk old.

Groups of five mice were anesthetized with Nembutal (sodium pentobarbital, 0.01 ml per g body weight) ip and their shaved ventral skin was exposed to a single dose of 2 kJ UVB radiation per $m^2$. Within 5 min of UV irradiation, the UV exposed skin was treated with Aloe extract in PBS or a control polysaccharide, methylcellulose (Sigma, St. Louis, Mo.) in PBS. Control animals were treated in an identical manner but were not exposed to UV radiation. Five days after sensitization, the mice were challenged by applying 5 µl of 0.5% fluoroscein isothiocyanate on both the dorsal and the ventral surfaces of each ear.

Systemic suppression of the DTH response was induced using a single exposure to UVB radiation as follows. The dorsal fur of the mice was shaved with electric clippers, the animals were put into cages with plexiglas dividers, one mouse per chamber, and the cage covered with a wire lid. The incident light received by the animals under these conditions was reduced to 2.6 W per $m^2$, by the shielding from the wire cage top. The animals were given a 5 kJ per $m^2$ dose of UVB radiation in a single exposure. Within 5 min of UV irradiation, the UV exposed skin was treated with Aloe extract, oligogalacturonides, or the tamarind seed xyloglucan oligosaccharides. Three days later, the mice were injected subcutaneously in each flank with $1\times10^7$ formalin fixed C. albicans cells. Ten days after sensitization, the mice were challenged with 50 µl of commercially prepared soluble Candida antigen, supplied as a 1:100 dilution (ALK Laboratories, Wallingford, Conn.) in each hind footpad. Footpad thickness (dorsal to plantar aspect) was measured immediately before challenge and 24 h later. Control mice were not sensitized with yeast cells but were challenged in both hind footpads with the Candida antigen. Specific footpad swelling was determined by subtracting the average values obtained from mice challenged but not sensitized.

The percentage restoration of immunity in UV irradiated animals treated with oligosaccharides was calculated using the following formula:

$$\frac{(\mu m \text{ swelling unirradiated Aloe treated}) - (\mu m \text{ swelling UV irradiated Aloe treated})}{\mu m \text{ swelling unirradiated Aloe treated}} \times 100\%$$

The response of UV irradiated, untreated mice was set as 0% restoration whereas values for unirradiated, Aloe treated groups were considered as 100% response.

UV radiation was administered in vivo using a bank of six unfiltered FS40 sunlamps (National Biological, Twinsburg, Ohio). Approximately 65% of the energy emitted from these lamps is within the UVB range (280–320 nm) and the peak emission is at 313 nm. The average irradiance of the source was ≈4.5 W per $m^2$ at 20 cm distance, as measured by an IL700 radiometer with an SEE280 filter and a W quartz diffuser (International Light, Newburyport, Mass.). A single FS-40 bulb was used to irradiate cultured keratinocytes. The output of the lamp was 4.7 J per $m^2$per s, at a tube-to-target distance of 23 cm.

EXAMPLE 5

SAPK/JNK Activation in Pam 212 Keratinocytes

Pam 212 transformed murine keratinocytes were grown on glass microscope slides as described in work from our laboratory (Byeon et al., 1998.) At the beginning of the study, the cells were washed in serum-free PBS. All subsequent treatments were done in serum-free PBS. Three groups of cells were exposed to 300 J/m² UVB from a single FS40 sunlamp. The UV-irradiated cells and unirradiated controls were washed 2× and 5 ml filter-sterilized PBS, Aloe barbadensis or tamarind xyloglucan in PBS was added to each culture. Following incubation for 30 min at 37° C., the cultures were washed 3× in PBS and stained with rabbit anti-phosphorylated JNK/SAPK and detected using an anti-rabbit second antibody and enzyme-substrate system (detection kits and reagents purchased from New England Biolabs, Beverly, Mass.). As shown in FIG. 1, the unirradiated cells exhibit a low background level of diffuse cytoplasmic staining. Following UV-irradiation, the phosphorylated (activated) JNK/SAPK proteins appear as a brown staining ring around the nucleus of the cells. *Aloe barbadensis* treatment partially reduced the activation (amount of staining observed.) Tamarind xyloglucan treatment of the UV-irradiated cells completely reduced the staining to background levels.

EXAMPLE 6 p38K Activation in Pam 212 Keratinocytes

Figure 2:
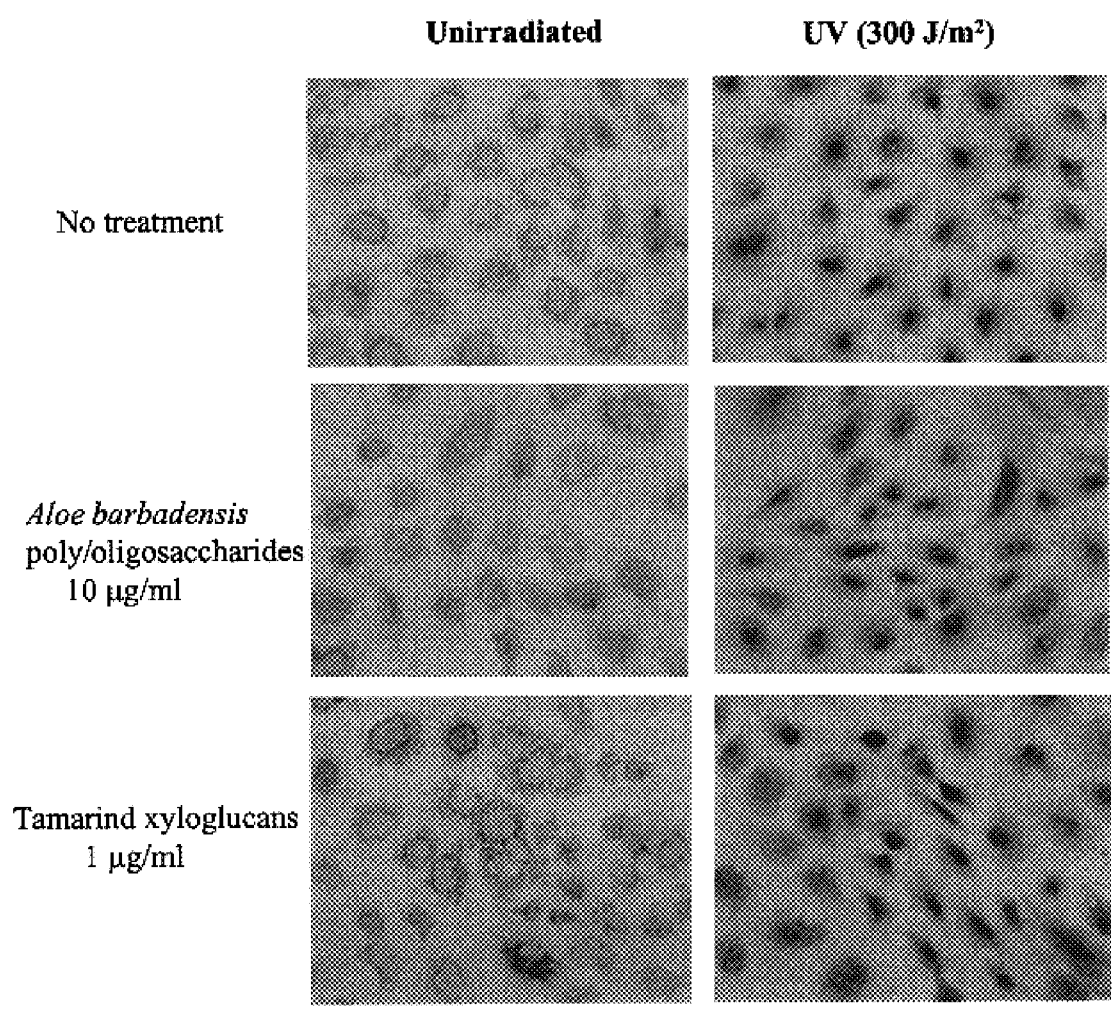
FIG. 2 shows p38K Activation in Pam 212 Keratinocytes. As shown, the unirradiated cells exhibit a low background level of perinuclear staining. Following UV-irradiation, the phosphorylated (activated) p38 proteins translocate to the nucleus and appear as a dearly staining nucleus. No compound had any effect on p38 activation. Therefore, the activity of the Aloe and tamarind appear to selectively affect some but not all of the signal transduction pathways activated by UV radiation.

Pam 212 transformed murine keratinocytes were grown on glass microscope slides as described in work from our laboratory (Byeon et al., 1998). At the beginning of the study, the cells were washed in serum-free PBS. All subsequent treatments were done in serum-free PBS. Three groups of cells were exposed to 300 J/m² UVB from a single FS40 sunlamp. The UV-irradiated cells and unirradiated controls were washed 2× and 5 ml filter-sterilized PBS, *Aloe barbadensis* or tamarind xyloglucan in PBS was added to each culture. Following incubation for 30 min at 37° C., the cultures were washed 3× in PBS and stained with rabbit anti-phosphorylated p38 stress activated protein kinase and detected using an anti-rabbit second antibody and enzyme-substrate system (detection kits and reagents purchased New England Biolabs, Beverly Mass.). As shown in FIG. 2, the unirradiated cells exhibit a low background level of perinuclear staining. Following UV-irradiation, the phosphorylated (activated) p38 proteins translocate to the nucleus and appear as a dearly staining nucleus. No compound had any effect on p38 activation. Therefore, the activity of the Aloe and tamarind appear to selectively affect some but not all of the signal transduction pathways activated by UV radiation.

EXAMPLE 7

Effect of Poly/Oligosaccharrides on Il-10 Protein in UV-irradiated Murine Skin

Figure 3:
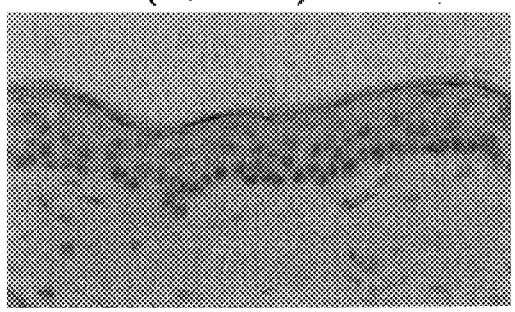
FIG. 3 shows the effect of poly/oligosaccharides on Il-10 Protein in UV-irradiated murine skin. The groups shown are: (i) animals that were treated with methylcellulose (5 μg/ml, 1 ml per mouse) following UVB injury—one section was not reacted with the anti-IL-10 but was reacted with the detection antibody and the substrate (no 1$^{(\ )}$Ab); (ii) animals treated with UVB only; (iii) animals which were treated with 1 μg/ml (1 ml/mouse) tamarind immediately after UVB irradiation; and (iv) animals that were treated with 1 μg oligogalacturonides following UVB irradiation.
Figure 3:
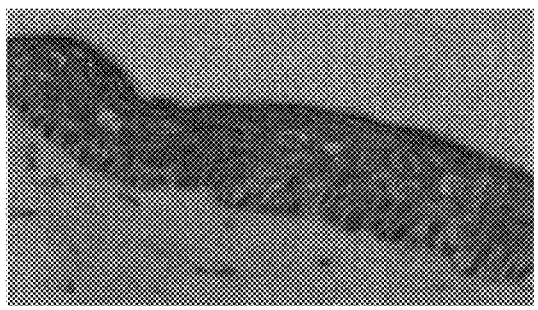
Figure 3:
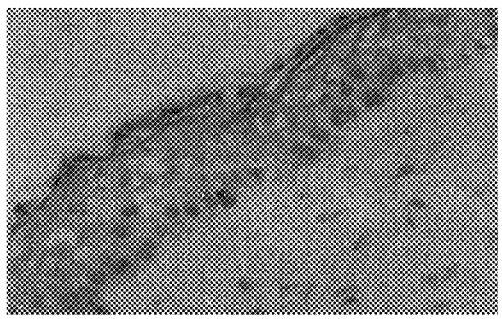
Figure 3:
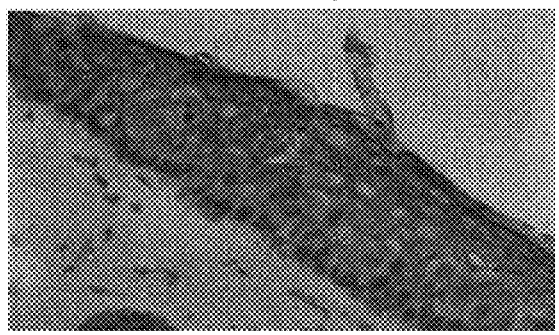
Figure 3:
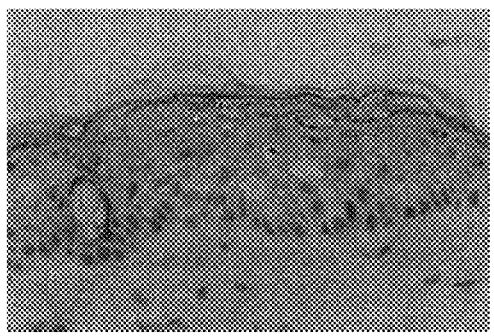

C3H female mice wee anesthetized and their shaved dorsal skin was exposed to 15 kJ/m² Ultraviolet B (UVB) radiation from a bank of FS40 sunlamps. Immediately after exposure, an unbuffered solution of methyl cellulose, oligogalacturonides, or tamarind xyloglucan oligosaccharide reconstituted in water was applied to the irradiated dorsal skin. After 4 days the mice were killed and their dorsal skin was removed. The subcutaneous fat was mechanically removed and the tissue was snap frozen and cryostat sections were made. The sections were stained with anti-murine Interleukin 10 (IL-10) monoclonal antibody (from rats) and detected using an anti-rate second antibody coupled to lactoperoxidase. Positive staining was detected using a calorimetric substrate (positive reactions stain brown). In FIG. 3, the groups shown are: (i) animals that were treated with methylcellulose (5 µg/ml, 1 ml per mouse) following UVB injury—one section was not reacted with the anti-IL-10 but was reacted with the detection antibody and the substrate (no 1$^{( \ )}$ Ab); (ii) animals treated with UVB only; (iii) animals which were treated with 1 µg/ml (1 ml/mouse) tamarind immediately after UVB irradiation; and (iv) animals that were treated with 1 µg oligogalacturonides following UVB irradiation.

All of the COMPOSITIONS and/or METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and/or METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patents

Baron, U.S. Pat. No. 4,788,007
Coats, U.S. Pat. No. 4,178,372
Coats, U.S. Pat. No. 5,356,811
Cobble, U.S. Pat. No. 3,892,853
Farkas, U.S. Pat. No. 3,103,466
Goldstein, U.S. Pat. No. 4,500,510
Gruber, U.S. Pat. No. 4,593,046
Kydiskis, U.S. Pat. No. 4,670,265
Lindauer et al., U.S. Pat. No. 4,627,934
Maret, U.S. Pat. No. 3,878,197
McAnalley, U.S. Pat. No. 4,851,25
McAnalley, U.S. Pat. No. 4,959,214
McAnalley, U.S. Pat. No. 4,966,892
McAnalley, U.S. Pat. No. 4,735,935
Rosenthal, U.S. Pat. No. 4,585,656
Strickland et al. U.S. Pat. No. 5,824,659

Pubilcations in the Scientific Literature

Albersheim and Darvill, "Oligosaccharins", *Scientific American*, 253: 58–64 (1985).

Andersen et al., "Ultraviolet B Dose-Dependent Inflammation in Humans: a Reflectance Spectroscopic and Laser Doppler Flowmetric Study Using Topical Pharmacologic Antagonists on Irradiated Skin", *Photodermatol., Photoimmunol. & Photomed.* 9:17–23 (1992)

Bauer, Talmadge, Keegstra, Albersheim, *Plant Physiol.*, 51:174–187, 1973.

Bax and Davis, *J. Magn. Reson.*, 65:355–360, 1985.

Bendall, Pegg, Doddrell, Field, *J. Magn. Reson.*, 51:520–526, 1983.

Bergstresser, "Sensitization and Elicitation of Inflammation in Contact Dermatitis", *Immunology Series*, 46:219–245 (1989)

Blumenkrantz and Asboe-Hansen, *Anal. Biochem.*, 54:484–489, 1973.

Bock, Pedersen, Pedersen, *Adv. Carbohydr. Chem. Biochem.*, 42:193–225, 1984.

Bodenhausen and Ruben, *Chem. Phys. Lett.*, 69:185–189, 1980.

Byeon, Pelley, Ullrich, Waller, Bucana, Strickland *J of Investigative Dermatology*, 110(5):811–817, 1998.

Darvill, Augur, Bergmann, Cheong, Eberhard, Hahn, Lò, Marfa, Meyer, Mohnen, O'Neill, Spiro, van Halbeek, York, Albersheim, *Glycobiology*, 2:181–198, 1992.

Davis et al., "Processed Aloe vera administered topically inhibits inflammation", *J. Amer. Podiatric Med. Assoc.* 79:395–397 (1987))

Davis, Darvill, Albersheim, Dell, *Plant Physiol.*, 80:568–577, 1986.

Dell and Tiller, *Biochem.. Biophys Res. Commun.*, 3:1126–1134, 1986.

Fernley, *J. Biochem.*, 87, 90–95, (1993)

Gowda "Structural studies of polysaccharides from *Aloe saponaria* and *Aloe vanbalenii*." *Carbohydrate Research* 83:402–405, 1980.

Gowda et al., "Structural studies of polysaccharides from Aloe vera" *Carb. Res.* 72:201–205, 1979.

Hadiabi, et al. "Structural studies of the glucomannan from *Aloe vahombe*." *Carbohydrate Research* 116: 166–170, 1983.

Hahn, Darvill, Albersheim, Bergmann, Cheong, Koller, Lò, *In: Molecular Plant Pathology (Vol. 2): A Practical Approach*, Gurr, McPherson, Bowles (Eds.), IRL Press, Oxford, pp 103–147.

Hahn, Darvill, Albersheim, *Plant Physiol.*, 68:1161–1169, 1981.

Hardy, Townsend, Lee, *Anal. Biochem.*, 170:54–62, 1988.

Hayashi, *Annu. Rev. Plant Physiol. Plant Mol. Biol.*, 40:139–168, 1989.

Hisamatsu, York, Darvill, Albersheim, *Carbohyd. Res.*, 227, 45–71, 1992.

Hotchkiss and Hicks, *Anal. Biochem.*, 184:200–206, 1990.

Kato, Matsushita, Kuboder, Matsuda, *Biochemistry*, 97:801–810, 1985.

Kennedy and How, *Carbohydr. Res.*, 28:13–19, 1973.

Kiefer, York, Albersheim, Darvill, *Carbohyd. Res.*, 197:139–158, 1990.

Kooiman, *Recl. Trav. Chim. Pays-Bas*, 80:849–865, 1961.

Kripke. "Effects of UV Irradiation on Tumor Immunity", *J. Natl. Canc. Inst. U.S.* pp 1392–1396 (1990)

Lee, *Anal. Biochem.*, 189:151–162, 1990.

Lee, *J. Invest. Dermatol.* 609–610 (1991).

Lò and van Halbeck, unpublished results

Mandal et al. "Characterization of polysaccharides of *Aloe barbadensis* Miller: Part III—Structure of an acidic oligosaccharide." *Ind. J. Chem.* 22B:890–893.

Mandal et al. "Structure of the D-galactan isolated from *Aloe barbadensis* Miller." *Carb. Res.* 86:247–257, 1980.

Mandal et al. "Structure of the glucomannan isolated from the leaves of *Aloe barbadensis* Miller." *Carb. Res.* 87:249–256, 1980.

Marfa, Gollin, Eberhard, Mohnen, Darvill, Albersheim, *Plant J.*, 217–225, 1991.

Marion and Wüthrich, *Biochem. Biophys. Res. Commun.*, 3:967–974, 1983.

McDougall and Fry, *Carbohydr. Res.*, 219:123–132, 1991.

McDougall and Fry, *Planta*, 175:412–416, 1988.

McNeil, Darvill, Fry, Albersheim, *Annu. Rev. Biochem.*, 53:625–663, 1984.

Mori, Eda, Kato, *Carbohydr. Res.*, 84:125–135, 1980.

Nothnagel, McNeil, Albersheim, Dell, *Plant Physiol.*, 71:916–926, 1983.

Otting and Wüthrich, *J. Magn. Reson.*, 76:569–574, 1988.

Paulsen, et al. "Structural studies of the polysaccharides from *Aloe plicatilis* Miller." *Carb. Res.* 60:345–351, 1978.

Pelley et al. "Aloe polysaccharides and their measurement." *Inside Aloe*, February 1996, Supplement, p 1–4.

Pressey, *Phytochemistry*, 32:1375–1379, 1993.

Pressey, *Plant Physiol.*, 96:1167–1170, 1991.

Radjabi-Nassab, et al. "Further studies of the glucomannan from *Aloe vahombe* (liliaceae). II. Partial hydrolyses and NMR $^{13}$C studies." *Biochimie* 66:563–567, 1984.

Rance, Sørensen, Bodenhausen, Wagner, Ernst, Wüthrich, *Biochem. Biophys. Res. Commun.*, 117:479–485, 1983.

Reeve et al., "The Protective Effect of Indomethacin on Photocarcinogenesis in Hairless Mice", *Cancer Letters*, 95:213–219 (1995)

Reeve et al., Differential Protection by Two Sunscreens from UV Irradiation-Induced Immunosuppression, *J. Invest. Dermatol.* 97:624–628 (1991)

Ring and Selvendran, *Phytochemistry*, 20(11):2511–2519, 1981.

Roboz et al.. "A Mucilage from Aloe Vera." *J. Am. Chem. Soc.* 70:3248–3249, 1948.

Roden, Baker, Cifonelli, Matthews, *Methods Enzymol.*, 28:73–140, 1972.

Ryan and Farmer, *Annu. Rev. Plant Physiol. Mol. Biol.*, 42:651–674, 1991.

Shaka, Barker, Freeman, *J. Magn. Reson.*, 64:547–552, 1985.

Solar, et al. *Arch. Inst. Pasteur Madagascar.* 47:1–31, 1979.

Strickland, Pelley, Kripke, "Prevention of ultraviolet radiation-induced suppression of contact and delayed hypersensitivity by *Aloe barbadensis* gel extract," *J. Invest. Dermatol.*, 102:197, 1994.

Tjan, Voragen, Pilnik, *Carb. Res.*, 34:15–23, 1974.

Vermeer et al., "Effects of Ultraviolet B Light on Cutaneous Immune Responses of Humans with Deeply Pigmented Skin", J. Invest. Dermatol., 97:729–734 (1991).

Von Praag et al., "Effect of Topical Sunscreens of the UV-Irradiation-Induced Suppression of the Alloactivating Capacity in Human Skin In Vivo", J. Invest. Dermatol., 97:629–633 (1991).

Wolf et al., "Analysis of the Protective Effects of Different Sunscreens on Ultraviolet Irradiation-Induced Local and Systemic Suppression of Contact Hypersensitivity and Inflammatory Responses in Mice", J. Invest. Dermatol. 100:254–259.

Womble et al., "Enhancement of allo-responsiveness of human lymphocytes by Acemannan (Carrisyn™)." *Int. J. Immunopharmac.* 10:967–974, 1988.

Yagi, et al. "Aloe mannan, polysaccharide, from *Aloe arborescens* var. *natalensis*." lanta Medica 31:17–20, 1977.

Yagi, et al. "Structure determination of polysaccharides in *Aloe saponaria* (Hill.) Haw. (Liliaceae)." *J. Pharmaceutical Sci.* 73: 62–65, 1984.

Yagi, et al., "Structure determination of polysaccharides in *Aloe arborescens* var. *natalensis.*" *Planta Medica* 213–218, 1986.

York, Darvill, Albersheim, *Plant Physiol.* 75:295–297, 1984.

York, Darvill, McNeil, Stevenson, Albersheim, *Methods Enzymol.*, 118:3–40, 1985.

York, Doubet, Darvill, Albersheim, *XIVth Int. Carbohyd. Symp.*, Stockholm, Sweden, Aug. 14–19, 1988, Abstr. no. A-9.

York, van Halbeek, Darvill, Albersheim, *Carbohyd. Res.*, 200:9–31, 1990.

What is claimed is:

1. A method of treating UV-induced suppression of the immune response of the skin of an animal, said method comprising contacting said skin with a composition comprising comprising tamarind seed xyloglucan oligosaccharides.

2. The method of claim 1, wherein said composition comprises an aqueous solution.

3. The method of claim 2, wherein said composition comprises said tamarind seed xyloglucan oligosaccharides at a concentration of at least $10^{-6}$ μg per mL of said solution.

4. The method of claim 1, wherein suppression of delayed type hypersensitivity is prevented.

5. The method of claim 1, wherein the amount of an interleukin-10 produced in said skin is reduced.

6. The method of claim 1, wherein said human is an animal.

7. A method of treating UV-induced suppression of the immune response of the skin of an animal, said method comprising administering to said animal an effective dose of a composition comprising tamarind seed xyloglucan oligosaccharides.

8. The method of claim 7, wherein said composition is administered orally.

9. The method of claim 7, wherein said composition is administered parenterally.

10. The method of claim 7, wherein said animal is a human.

* * * * *